US010100321B2

(12) United States Patent
Chua et al.

(10) Patent No.: US 10,100,321 B2
(45) Date of Patent: Oct. 16, 2018

(54) METHODS FOR INCREASING COTTON FIBER LENGTH

(75) Inventors: Nam-Hai Chua, Singapore (SG); Jian Ye, Singapore (SG); Jing Qu, Singapore (SG)

(73) Assignee: TEMASEK LIFE SCIENCES LABORATORY LIMITED, Singapore (SG)

( * ) Notice: Subject to any disclaimer, the term of this patent is extended or adjusted under 35 U.S.C. 154(b) by 817 days.

(21) Appl. No.: 14/395,233

(22) PCT Filed: Apr. 19, 2012

(86) PCT No.: PCT/SG2012/000139
§ 371 (c)(1),
(2), (4) Date: Oct. 17, 2014

(87) PCT Pub. No.: WO2013/158032
PCT Pub. Date: Oct. 24, 2013

(65) Prior Publication Data
US 2015/0074853 A1    Mar. 12, 2015

(51) Int. Cl.
*C12N 15/82* (2006.01)
*C07K 14/415* (2006.01)

(52) U.S. Cl.
CPC ........ *C12N 15/8218* (2013.01); *C07K 14/415* (2013.01); *C12N 15/8234* (2013.01); *C12N 15/8247* (2013.01); *C12N 15/8261* (2013.01); *Y02A 40/146* (2018.01)

(58) Field of Classification Search
None
See application file for complete search history.

(56) References Cited

U.S. PATENT DOCUMENTS

| 2004/0133944 A1* | 7/2004 | Hake | C12N 15/8247 800/281 |
| 2007/0061916 A1* | 3/2007 | Kovalic | C07K 14/415 800/278 |
| 2011/0162103 A1* | 6/2011 | Hartel | C07K 14/415 800/281 |

FOREIGN PATENT DOCUMENTS

| WO | 2004063333 A2 | 7/2004 |
| WO | 2006133441 A2 | 12/2006 |
| WO | 2010/144058 A1 | 12/2010 |

OTHER PUBLICATIONS

Maeo et al (An AP2-type transcription factor, WRINKLED1, of *Arabidopsis thaliana* binds to the AW-box sequence conserved among proximal upstream regions of genes involved in fatty acid synthesis. The Plant Journal 60, 476-487, 2009).*

(Continued)

*Primary Examiner* — Medina A Ibrahim
*Assistant Examiner* — Wayne Zhong
(74) *Attorney, Agent, or Firm* — Rothwell, Figg, Ernst & Manbeck, P.C.

(57) ABSTRACT

The present invention relates to the field of plant molecular biology, more particularly cotton WRINKLED 1-like (WREL) genes. More specifically, the present invention relates to cotton WRIL genes whose products act as transcription factors of genes involved in fatty acid biosynthesis. The present invention also relates to methods of increasing cotton fiber length in cotton. In one embodiment, the methods involve modulating the level of activity of an enzyme involved in a fatty acid biosynthesis in the host cotton cell and/or culturing the host cotton cell. In another embodiment, the methods involve the manipulation of transcription factors which can regulate an enzyme involved in fatty acid biosynthesis.

10 Claims, 12 Drawing Sheets

Specification includes a Sequence Listing.

(56) References Cited

OTHER PUBLICATIONS

Chaudhary et al (Global analysis of gene expression in cotton fibers from wild and domesticated Gossypium barbadense. Evolution & Development 10:5, 567-582, 2008).*

Chinese Office Action and English Translation dated Apr. 26, 2016, Chinese Application No. 201280074075.3, 12 pages.

Xu, Shou-Min et al., "Overexpression of a Potato Sucrose Synthase Gene in Cotton Accelerates Leaf Expansion, Reduces Seed Abortion, and Enhances Fiber Production," Molecular Plant, vol. 5, No. 2, pp. 430-441, Mar. 2012, 12 pages.

Jiang, Yanjie et al., "Overexpression of GhSusA1 Increases Plant Biomass and Improves Cotton Fiber Yield and Quality," Plant Biotechnology Journal (2012), 10, pp. 301-312, 12 pages.

Chapman, Kent D. et al., "Compartmentation of Triacylglycerol Accumulation in Plants," The Journal of Biological Chemistry, vol. 287, No. 4, pp. 2288-2294, Jan. 20, 2012, 8 pages.

Maeo, Kenichiro et al., "An AP2-type Transcription Factor, WRINKLED1, of *Arabidopsis thaliana* Binds to the AW-Box Sequence Conserved Among Proximal Upstream Regions of Genes Involved in Fatty Acid Synthesis," The Plant Journal (2009), 60, pp. 476-487, 12 pages.

European Search Report and Written Opinion dated Nov. 27, 2015, Application No. 12874457.0-1410 / 2839007 PCT/SG2012000139, Temasek Life Sciences Laboratory Limited, 10 pages.

Udall, J.A. et al., "A Global Assembly of Cotton ESTs," Genome Research, 2006, vol. 16, pp. 441-450, © 2006, Published by Cold Spring Harbor Laboratory Press.

Qin, Yong-Mei et al., "Saturated Very-Long-Chain Fatty Acids Promote Cotton Fiber and *Arabidopsis* Cell Elongation by Activating Ethylene Biosynthesis," The Plant Cell, Nov. 2007, vol. 19, pp. 3692-3704, © 2007 American Society of Plant Biologists.

Gou, Jin-Ying et al., "Gene Expression and Metabolite Profiles of Cotton Fiber During Cell Elongation and Secondary Cell Wall Synthesis," Cell Research, 2007, vol. 17, pp. 422-434, © 2007 IBCB, SIBS, CAS.

PCT International Search Report, dated Jun. 18, 2012, International Application No. PCT/SG2012/000139, Filing date: Apr. 19, 2912; Applicant: Temasek Life Sciences Laboratory, 8 pages.

* cited by examiner

FIG. 1A

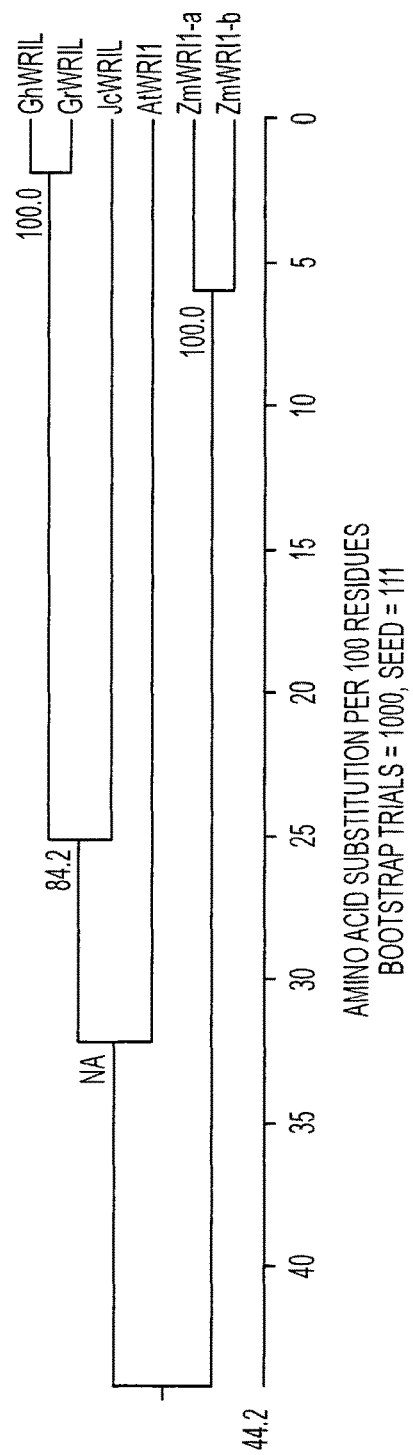

```
                      1580         *        1600         *        1620         *        1640         *        1660         *        1680
AtACCase1  : GMVAWCLDMSTPEFPMGRKLLIVIANDVTFKAGSFGPREDAFFIAVTELACAKKLPLIYLAANSGARLIGVAEEVVACFKVGWSDEISPEMGFQYIYLSPEDHERIG :  1680
GhACCase1  : ---------------------------------SFGPREDAFFLAVTDLACSKKLPLIYLAANSGARIGVAEEVVACFKVGWSNESSPERGFQYVYLTPEDYTKIG :    73

*        1700         *        1720         *        1740         *        1760         *        1780
AtACCase1  : SSVIAHEVKLSSGETRWVIDTIVGKEDGIGVENLTGSGAIAGAYSKAVNETFTLTFVSGRTVGIGAYLARLGMRCIQRLDQPIILTGFSTLNKLLGREVYSSHMQ :  1785
GhACCase1  : SSVIAHEMKLASGESRWVIDTIVGKEDGIGVENLTGSGAIAGAYSRAVRETFTLTYVTGRTVGIGAYLARLGMRCIQRLDQPIILTGFSALNKLLGREVYSSHMQ :   178

*        1800         *        1820         *        1840         *        1860         *        1880
AtACCase1  : LGGPKIMGTNGVVHLTVSDDLEGVSAILNWLSYIPAYVGGPLPVLAPLDPPERIVEVYPENSCDPRAATAGVAKDNTIGKWLGGIFDKNSFIETLEGMARIVVTGRA :  1890
GhACCase1  : LGGPKIMATNGVVHLTVSDDLEGVSAILNWLSCIPHIGGPLPILNPSDPPERLVEVLPENSCDPRAAISGALDSSGNMWKGGIFDRDSFVETLEGMARIVVTGRA :   283

*        1900         *        1920         *        1940         *        1960         *        1980
AtACCase1  : KLGGIPVGVIVAVETQTVMQIIPADPGQLDSHERVVPQAGQVWFPDSAAKTAQAALMDFNREELPLFIIANWRGFSGGQRDLFEGILQAGSTIVENLRTYRQPVFVY :  1995
GhACCase1  : KLGGIPVGIVAVETQVMQVIPADPGQLDSHERVVPQAGQVWFPDSAIKTAQAIMDFNREELPLFIIANWRGFSGGQRDLFEGILQAGSTIVENLRTYKQPVFVY :   388

*        2000         *        2020         *        2040         *        2060         *        2080
AtACCase1  : IPMGELRGGAWVVVDSQINSDYVEMYADETARGNVLEPGTIEIKFRTKELLECMGRLDQKLISLKAKLQDAKQSEAYAVANTELLQQQIRAREKQLLPVIIQIAT :  2100
GhACCase1  : IPMGELRGGAWVVVDSRINSDHIEMYAERTAKGNVLEPFGMIEIKFRTKELLECMGRLDQOLINMKAKLQEAKSNGAHAQMDSLQQQIRSREKQLLPVTQIAT :   493

*        2100         *        2120         *        2140         *        2160         *        2180         *        2200
AtACCase1  : KFAELHDTSMRMAAKGVIKSVVEMSGSRSFFYKKLNRRIAFSSLVKNVREASGDNLAYKSSMRLIQDWFCNSDIAKGKEEAWDDOVFFTWKDNVSNYELKLSEEL :  2205
GhACCase1  : KFAELHDTSLRMAAKGVIKEVVDMDRSRSFFYRLRRRIAFSSLVKIVKNAAGDQLSMKSARDIIRKGFLDSSVAKGREDVMNDEAFFSWDDLGNYSEKLQEEL :   598

*        2220         *        2240
AtACCase1  : RAQKLINQLAETGNSS-DLQALPQGLANTLINWVEPSKREELVAAIRKVLG- :  2254
GhACCase1  : RVQKVILQLMNIGNSSSDIQTLPQGLAALLSKMEPSSRKQMVDELRKVLG- :   648
```

FIG. 7

```
             *         20         *         40         *         60         *         80         *        100         *
AtKASI : MQALQSSSLIRASPPNPLRLIPSNRQSHQLITNARPLRRQORSFITSASASTVSAPKRETDPKKRVVITGMGLVSVFGNDVDAYYEKLLSGESGISLIDRFDASKFPTRFGGQI : 111
GhKASI : MEALQASSLRASPLKPLQKPKLNIHFPNASRLVPRPFKKFSSSITASSPTVSAPKREKDPKKRVVITGMGLVSVFGNDVDAYYDKLLAGESGIGLIDRFDASKFPTRFAGQL : 111

*        120         *        140         *        160         *        180         *        200         *        220
AtKASI : RGFSSEGYIDGKNERRLDDCLKYCIVAGKKALESANLGDDKINTIDKRRAGVLVGTGMGGLTVFSEGVQNLIEKGHRRISPFFIPYAITNNGSALLAIDIGLMGPNYSIST : 222
GhKASI : RGFSSQGYIDGKNDRRLDDCLRYCIVAGKKALEDADLGGDKLSKIDKERAGVLVGTGMGGLTVFSPDGVQNLIEKGYRKITPFFIPYAITNMSSALLAIDIGLMGPNYSIST : 222

*        240         *        260         *        280         *        300         *        320         *
AtKASI : ACATSNYCFYAAANHIRRGEADMMIAGGTEAAIIPIGLGGFVACRALSQRNDDPQTASRPWDKARDGFVMGEGAGVIVMESLEHAMKRGAPIVAEYLGGAVNCDAHHMTDP : 333
GhKASI : ACATSNYCFYAAANHIRRGEAEMMIAGGTEAAIIPIGLGGFVACRALSQRNDDPQTASRPWDKDRDGFVMGEGAGVIVMESLEHAMKRGAPIIAEYLGGAVNCDAYHMTDP : 333

*        340         *        360         *        380         *        400         *        420         *        440
AtKASI : RADGLGVSSCIERQLEDAGVSPEEVNYINAHATSTLAGDLAEINAIKKVFKSTSGIKINATKSMIGHCLGAAGGLEAIATVKAINTGWLHPSINQFNPEQAVDFDTVPNEK : 444
GhKASI : RADGLGVSSCIERSLEDAGVSPEEVNYINAHATSTLAGDLAEINAIKKVFKNTSEIKINATKSMIGHCLGAAGGLEAIATVKAITTGWVHPTINQFNPEPSVEFDTVANEK : 444

*        460         *
AtKASI : KQHEVDVAISNSTGFGGHNSVVAFSAFKP : 473
GhKASI : QQHEVNVAISNSRFGGHNSVVAFSAFKP  : 473
```

METHODS FOR INCREASING COTTON FIBER LENGTH

CROSS-REFERENCE TO RELATED APPLICATIONS

The present application is a national stage filing under 35 U.S.C. § 371 of PCT/SG2012/000139, filed on 19 Apr. 2012, which is incorporated herein by reference in its entirety.

SEQUENCE SUBMISSION

The present application is being filed along with a Sequence Listing in electronic format. The Sequence Listing is entitled 2577215PCTSequenceListing.txt, created on 18 Apr. 2012 and is 95 kb in size. The information in the electronic format of the Sequence Listing is incorporated herein by reference in its entirety.

BACKGROUND OF THE INVENTION

The present invention relates to the field of plant molecular biology, more particularly cotton WRINKLED1-like (WRIL) genes whose encoded proteins act as transcription factors of genes involved in fatty acid biosynthesis. The present invention also relates to methods of increasing cotton fiber length in cotton. In one embodiment, the methods involve modulating the level of activity of an enzyme involved in a fatty acid biosynthesis in the host cotton cell and/or culturing the host cotton cell. In another embodiment, the methods involve the manipulation of transcription factors which can regulate a gene encoding an enzyme involved in fatty acid biosynthesis.

The publications and other materials used herein to illuminate the background of the invention or provide additional details respecting the practice, are incorporated by reference, and for convenience are respectively grouped in the Bibliography.

Cotton (*Gossypium* spp.) is the world's most important fiber plant and a significant oilseed crop, being grown in more than 80 countries with a record of 122 million 480-pound bales in world production during the 2006/2007 growing season (United States Department of Agriculture—FOREIGN Agricultural Service). The deficit between consumption and production has happened in 1994/1995 and is forecasted to continue to widen to 2.5 million 480-pound bales in the 2009/2010 growing season (United. States Department of Agriculture—Foreign Agricultural Service [USDA—FAS] 2009). Cotton production provides income for approximately 100 million families, and approximately 150 countries are involved in cotton import and export. Its economic impact is estimated to be approximately $500 billion/year worldwide. Moreover, modifying cotton-seed for food and feed could profoundly enhance the nutrition and livelihoods of millions of people in food-challenged economies. Cotton is also a potential candidate plant of renewable biofuel. Cotton fiber is composed of nearly pure cellulose. Compared to lignin, cellulose is easily convertible to biofuels. Optimized cotton fiber production and processing will ensure that this natural renewable product will be competitive with petroleum-derived synthetic non-renewable fiber to ensure more sustainable development.

At present, seeds are always the most important part used for human and animal nutrition for crops. Major seed storage compounds include such as triacylglycerol (TAG), proteins, and carbohydrates, which are typically making up most of the mass of mature seeds, and the proportions of these components have large species-specific variations. Since seed composition and yield are important traits for breeding and agricultural research, partitioning of carbon and nitrogen into the major storage products within the developing seed is an important process. In model plant *Arabidopsis*, one AP2-domain containing transcription factor WRINKLED1 (WRI1; At3g54320) controls the conversion of sucrose into triacylglycerol and showed a strong role in controlling carbon and nitrogen flux into TAG biosynthesis and accumulation (Cernac and Benning, 2004).

As the most important agronomic traits of cotton are fiber quality and yield it is important to improve our understanding of genes underlying cotton fiber development. Cotton fibers are single-celled seed trichomes and the developing cotton fiber is considered as an excellent model system for studying the dynamics and functions of the cytoskeleton (Seagull, 1990). It is important to investigate how dynamic changes of the cytoskeleton and the expression of cytoskeleton-related genes contribute to fiber development. Some progress has been made in this direction. GhActin, a cyto-skeleton protein, has been proven to be important for fiber elongation but not fiber initiation (Li et al., 2005). Overexpression of a fiber-preferential actin-binding protein (Gh-PFN2) blocked cell elongation prematurely (Wang et al., 2010). On the other hand, down-regulation of the actin depolymerizing factor gene (ADF) has been reported to increase fiber length and fiber strength (Wang et al., 2009).

The ultimate objective of gene function analysis in cotton is to utilize them to increase cotton fiber yield and quality. At present, there are relative few genes which have been successfully used to transform cotton and increase cotton fiber yield and quality. Many of them come from carbohydrate biosynthesis genes. For example, the transgenic overexpression of sucrose synthase gene (sus and sps) and cellulose synthesis gene (acsA and acsB) improved cotton fiber length and strength (Ruan et al., 2003; Jiang et al., 2011;). Similarly, higher xyloglucan endotransglycosylase/hydrolase (XTH) activity can promote fiber cell elongation and transgenic cotton with over-expressed xth gene had increased mature fiber length (Lee et al., 2010). The overexpression of carbohydrate biosynthesis genes may partition fixed carbon toward carbohydrates thus increase cotton fiber yield and quality. It is interesting to find some transcriptional factors which can regulate the carbon flow between lipids and carbohydrates in reproductive organs of cotton. Work with *Arabidopsis* has shown that over-expression of an *Arabidopsis* WRI1 cDNA under the control of the cauliflower mosaic virus 35S promoter led to increased seed oil content (Cernac and Benning, 2004). On the other hand, seed oil accumulation in an *Arabidopsis* splicing mutant allele, wri1-1, was reduced. Glycolysis was compromised in this mutant, rendering developing embryos unable to efficiently convert sucrose into precursors of triacylglycerol biosynthesis (Cernac and Benning, 2004).

The availability of genetic resources and cotton gene sequences will facilitate the improvement of key agronomic traits of cotton. To this end, a public effort was initiated in 2007 to determine the complete cotton genomic sequence. While this effort is underway there is an ever-expanding set of *Gossypium* EST sequences (about 400,000 now) being deposited in the public database. Notwithstanding the availability of such a huge amount of cotton gene sequences the functions of only a small number of genes have been identified. This is mainly because large scale analysis of cotton gene function has been constrained by the laborious and time-consuming process of generating transgenic cotton. Moreover, many cotton cultivars are recalcitrant to genetic transformation. Therefore, there is an urgent need to develop a rapid method for species independent functional analysis of *Gossypium* genes on a genomic scale.

Virus-induced gene silencing (VIGS) offers an attractive alternative to transgenic technology as it allows the investigation of gene functions without plant transformation (Ruiz et al., 1998; Burch-Smith et al., 2004). A partial fragment of a candidate gene is inserted into the virus vector to generate a recombinant virus. Infection of plants with this recombinant virus leads to the production of virus-related small interfering RNAs (siRNAs) (Baulcombe, 2004), which can mediate degradation of related endogenous gene transcripts, resulting in silencing of the candidate gene expression in inoculated plants (Brigneti et al., 2004; Burch-Smith et al., 2004). The silencing effect on endogenous gene expression can usually be assayed 1-2 weeks after virus inoculation. VIGS has become one of the most widely used and indeed important reverse genetics tools, especially for non-model plants.

It is desired to identify genes that are involved in biosynthetic pathways that the modulation of which may lead to increased cotton fiber length. It is also desired to develop methods for increasing cotton fiber length.

SUMMARY OF THE INVENTION

The present invention relates to the field of plant molecular biology, more particularly cotton WRINKLED1-like (WRIL) genes. More specifically, the present invention relates to cotton WRIL genes whose products act as transcription factors of genes involved in regulating fatty acid biosynthesis. The present invention also relates to methods of increasing cotton fiber length in cotton. In one embodiment, the methods involve modulating the level of activity of an enzyme involved in a fatty acid biosynthesis in the host cotton cell and/or culturing the host cotton cell. In another embodiment, the methods involve the manipulation of transcription factors which can regulate a gene encoding an enzyme involved in fatty acid biosynthesis.

In a first aspect, the present invention provides an isolated nucleic acid encoding a GrWRIL protein comprising the amino acid sequence set forth in SEQ ID NO:2. In one embodiment, the nucleic acid comprises the nucleotide sequence set forth in SEQ ID NO:1. In another embodiment, the nucleic acid comprises the nucleotide sequence set forth as nucleotides 25-1338 of SEQ ID NO:1. In an additional embodiment, the nucleic acid comprises the nucleotide sequence set forth as nucleotides 25-1341 of SEQ ID NO:1. In a further embodiment, the nucleic acid further comprises a plant operable promoter operably linked to the nucleic acid. In one embodiment, the promoter is a seed specific promoter. In another embodiment, the seed specific promoter is a cotton seed specific promoter.

In a second aspect, the present invention provides an isolated nucleic acid encoding a GrWRIL protein comprising the amino acid sequence set forth in SEQ ID NO:4. In one embodiment, the nucleic acid comprises the nucleotide sequence set forth in SEQ ID NO:3. In another embodiment, the nucleic acid comprises the nucleotide sequence set forth as nucleotides 32-1345 of SEQ ID NO:3. In an additional embodiment, the nucleic acid comprises the nucleotide sequence set forth as nucleotides 32-1348 of SEQ ID NO:3. In a further embodiment, the nucleic acid further comprises a plant operable promoter operably linked to the nucleic acid.

In one embodiment, the promoter is a seed specific promoter. In another embodiment, the seed specific promoter is a cotton seed specific promoter.

In a third aspect, the present invention provides a construct or vector comprising an isolated nucleic acid as described herein. In one embodiment, the construct or vector is an expression construct or vector. In another embodiment, the construct or vector further comprises a selectable marker. In a further embodiment, the construct or vector comprises a Cre-lox recombination marker free system.

In a fourth aspect, the present invention provides a transgenic plant comprising a nucleic acid or vector described herein. In one embodiment, the transgenic plant is a cotton plant.

In a fifth aspect, the present invention provides for the down regulation of a cotton WRIL gene. In one embodiment, the down regulation of a cotton WRIL gene involves using RNA interference (RNAi), including microRNA and hairpin RNA. In another embodiment, the down regulation of a cotton WRIL gene involves using viral induced gene silencing (VIGS). In one embodiment, a nucleic acid is provided which down regulates the GhWRIL gene. In another embodiment, a nucleic acid is provided which down regulates the GrWRIL gene. In one embodiment, the nucleic acid further comprises a plant operable promoter operably linked to the nucleic acid. In one embodiment, the promoter is a seed specific promoter. In another embodiment, the seed specific promoter is a cotton seed promoter. According to this aspect, the present invention also provides a vector comprising an isolated nucleic acid as described herein. In one embodiment, the vector is an expression vector. In another embodiment, the vector further comprises a selectable marker. In a further embodiment, the vector comprises a Cre-lox recombination marker free system. According to this aspect, the present invention further provides a transgenic or infected plant comprising a nucleic acid or vector described herein. In one embodiment, the transgenic or infected plant is a cotton plant.

In a sixth aspect, the present invention provides methods of increasing cotton fiber length in cotton. In one embodiment, a method involves modulating the level of activity of an enzyme involved in fatty acid biosynthesis in the host cotton cell and/or culturing the host cotton cell. In one embodiment, the enzyme is acetyl-CoA carboxylase (ACCase), β-ketoacyl-acyl carrier protein synthase. I (KASI) or enoyl-acyl carrier protein reductase (ENR). In another embodiment, a method involves the manipulation of transcription factors which can regulate an enzyme involved in fatty acid biosynthesis. In one embodiment, the transcription factor is a cotton WRIL protein. In another embodiment the cotton WRIL protein is a GhWRIL protein or a GrWRIL protein.

BRIEF DESCRIPTION OF THE FIGURES

FIGS. 1A and 1B show amino acid sequence alignment (FIG. 1A) and phylogenetic tree (FIG. 1B) of WRI1-like proteins. AtWRI1 protein sequence can be accessed from GenBank Accession No. AAP80382 and is set forth in SEQ ID NO:5. GhWR1-like (GhWRIL), a *Gossypium hirsutum* (upland cotton, tetraploid) WRIL homolog, protein sequence is set forth in SEQ ID NO:2. GrWRIL, another WRIL homolog from wild cotton *Gossypium raimondii* (one of the putative progenitor species of tetraploid cotton), protein sequence is set forth in SEQ ID NO:4. JcWRIL, a *Jatropha curcas* WRIL homolog, protein sequence can be accessed from International application publication NO. WO 2010/

071608, and is set forth in SEQ ID NO:6. ZmWRI1-a, a *Zea mays* WRI1 homolog, protein sequence can be accessed from GenBank Accession No. ACG32367 and is set forth in SEQ ID NO:7. ZmWRI1-b, another *Zea mays* WRI1 homolog, protein sequence can be accessed from GenBank Accession No. NP_001131733 and is set forth in SEQ ID NO:8.

Figure 2:
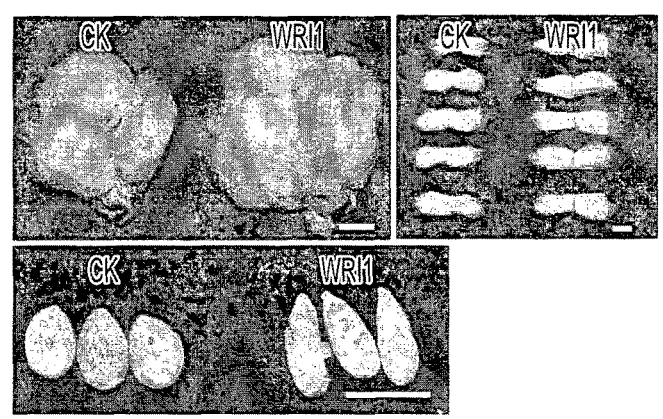
Figure 3:
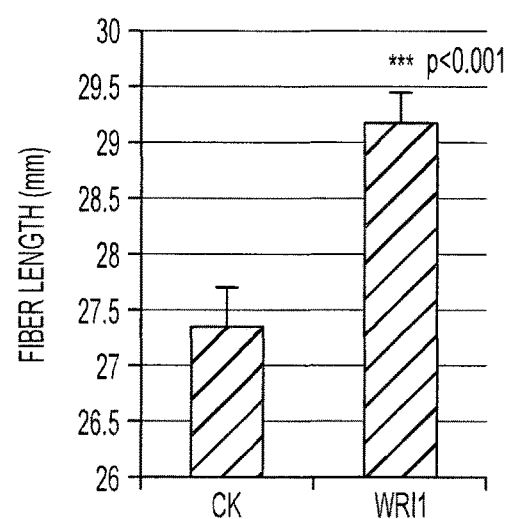

FIG. 2 shows phenotypes of vector control (CK) and WRI1-silenced cotton bolls and seeds FIG. 3 shows the longer fiber on WRIT-silenced cotton bolls (P<0.001) compared with CK bolls.

Figure 4:
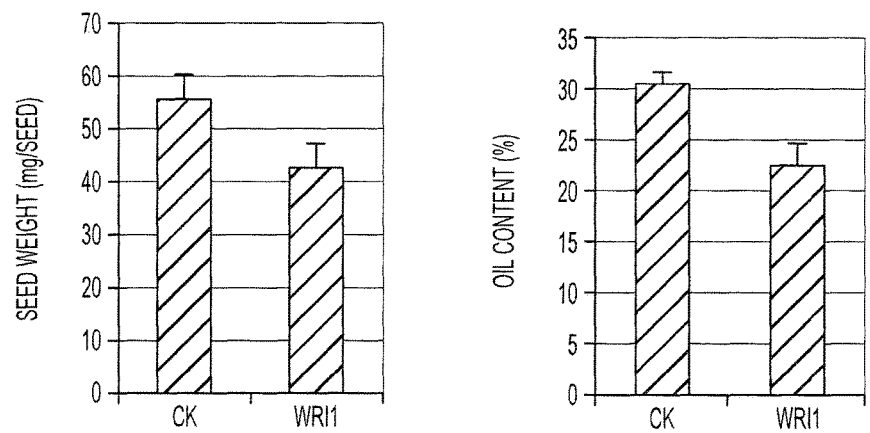

FIG. 4 shows that both seed weight and oil content reduced in GhWRIL-silenced cotton seed.

Figure 5:
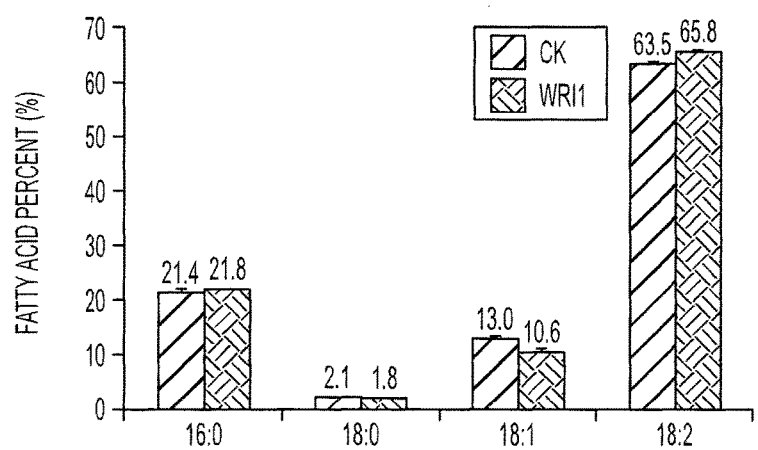

FIG. 5 shows that fatty acid profile changed in GhWRIL-silenced cotton seed.

Figure 6:
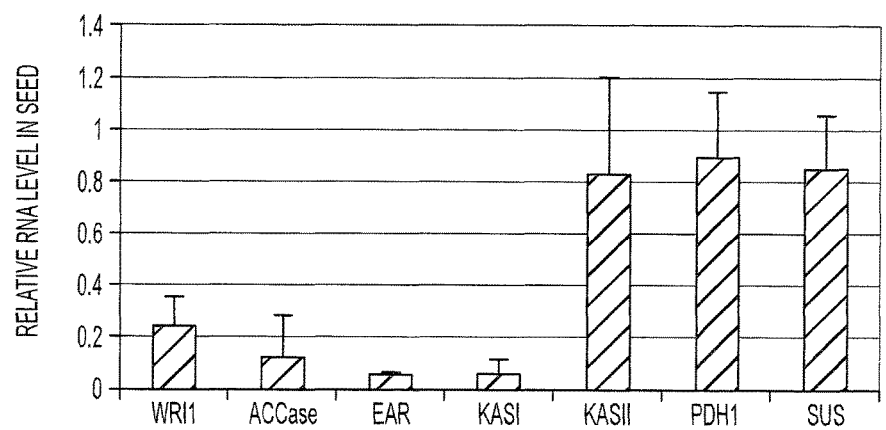

FIG. 6 shows the down-regulation of fatty acid biosynthesis genes in GhWRIL-silenced cotton seed.

FIG. 7 shows the partial acetyl-CoA carboxylases protein sequence alignment between *Gossypium hirsutum* (SEQ ID NO:10) and *Arabidopsis thaliana* (SEQ ID NO:11).

Figure 8B:
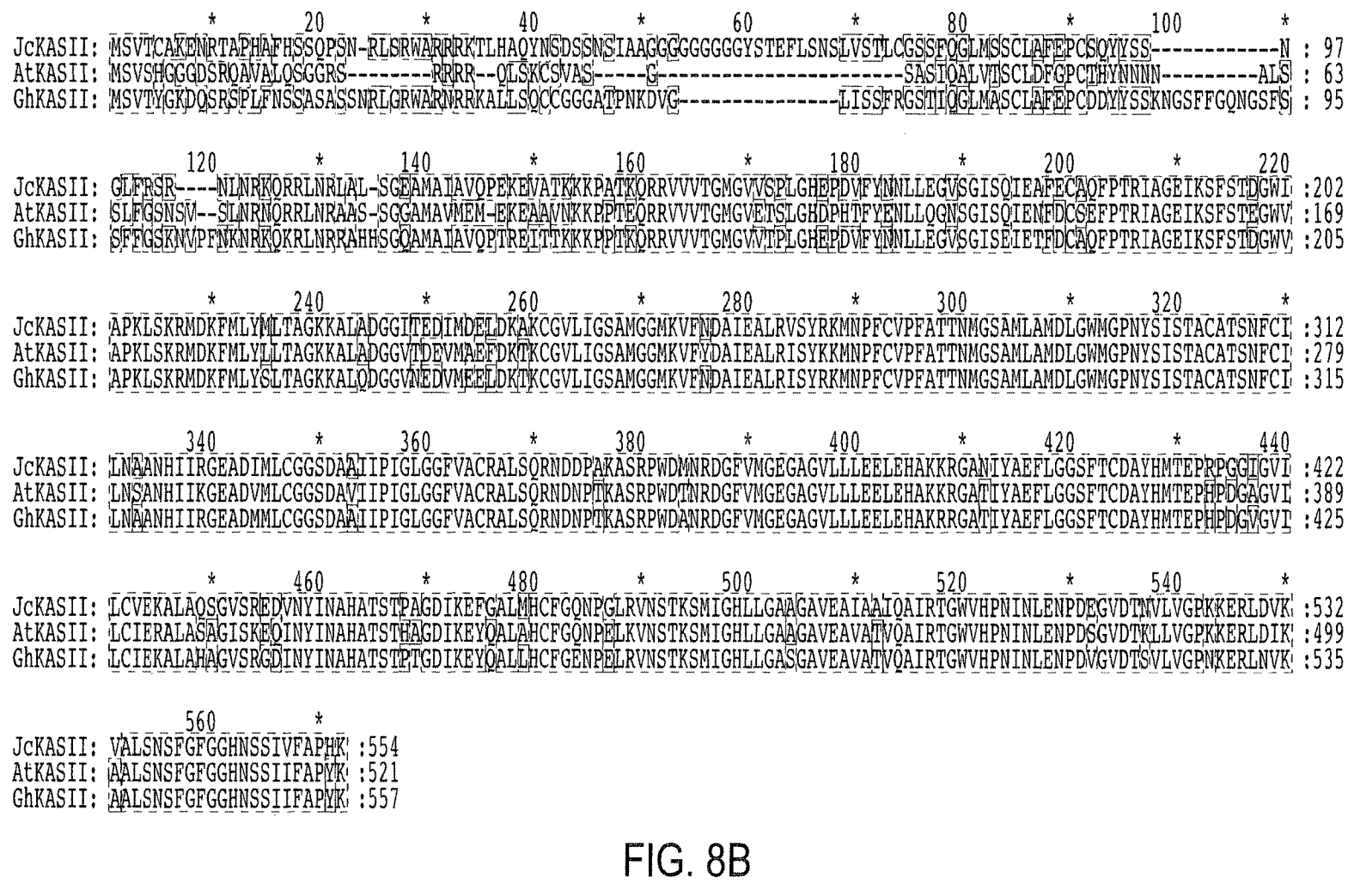

FIGS. 8A and 8B show the KASI and KASII protein sequence alignments. FIG. 8A shows the alignment for *Gossypium hirsutum* (SEQ ID NO:13) and *Arabidopsis thaliana* (SEQ ID NO:14) KASI. FIG. 8B shows the alignment for *Gossypium hirsutum* (SEQ ID NO:16), *Arabidopsis thaliana* (SEQ ID NO:17) and *Jatropha curcas* (SEQ ID NO:18) KASII.

Figure 9A:
Figure 9B:
Figure 9C:
Figure 9D:
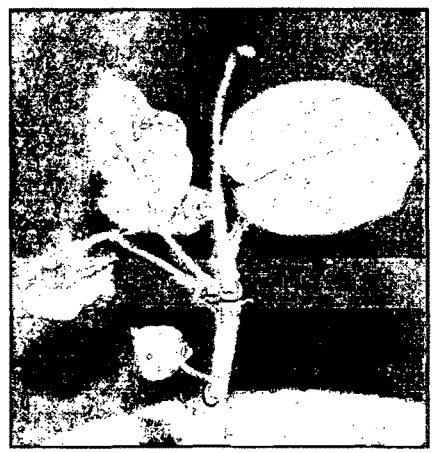
Figure 10A:
Figure 10C:
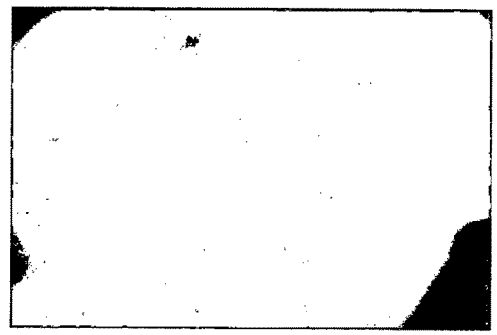
Figure 10B:
Figure 10D:
Figure 10E:

FIGS. 9A-9D show severe phenotypes in acetyl-CoA carboxylase gene silenced cotton plants. FIG. 9A: sTRV1+sTRV2 vector control treated cotton plants. FIGS. 9B-9D: sTRV1+sTRV-GhACCase1 treated cotton plants.

FIGS. 10A-10E show severe phenotypes of key gene of fatty acid elongation KASI and KASII silenced cotton plants.

DETAILED DESCRIPTION OF THE INVENTION

The present invention relates to the field of plant molecular biology, more particularly cotton WRINKLED1-like (WRIL) genes. More specifically, the present invention relates to cotton WRIL genes whose products act as transcription factors of genes involved in fatty acid biosynthesis. The present invention also relates to methods of increasing cotton fiber length in cotton. In one embodiment, the methods involve modulating the level of activity of an enzyme involved in a fatty acid biosynthesis in the host cotton cell and/or culturing the host cotton cell. In another embodiment, the methods involve the manipulation of transcription factors which can regulate an enzyme involved in fatty acid biosynthesis.

Unless defined otherwise, all technical and scientific terms used herein have the same meaning as is commonly understood by one of skill in the art to which the invention belongs.

As used herein, "allele" refers to any of one or more alternative forms of a gene locus, all of which alleles relate to a trait or characteristic. In a diploid cell or organism, the two alleles of a given gene occupy corresponding loci on a pair of homologous chromosomes.

As used herein, "gene" refers to a nucleic acid sequence that encompasses a 5' promoter region associated with the expression of the gene product, any intron and exon regions and 3' or 5' untranslated regions associated with the expression of the gene product.

As used herein, "genotype" refers to the genetic constitution of a cell or organism.

As used herein, "phenotype" refers to the detectable characteristics of a cell or organism, which characteristics are the manifestation of gene expression.

The terms "polynucleotide," nucleic acid" and "nucleic acid molecule are used interchangeably herein to refer to a polymer of nucleotides which may be a natural or synthetic linear and sequential array of nucleotides and/or nucleosides, including deoxyribonucleic acid, ribonucleic acid, and derivatives thereof. It includes chromosomal DNA, self-replicating plasmids, infectious polymers of DNA or RNA and DNA or RNA that performs a primarily structural role. Unless otherwise indicated, nucleic acids or polynucleotide are written left to right in 5' to 3' orientation, Nucleotides are referred to by their commonly accepted single-letter codes. Numeric ranges are inclusive of the numbers defining the range.

The terms "polypeptide," "peptide," and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. Amino acids may be referred to by their commonly known three-letter or one-letter symbols. Amino acid sequences are written left to right in amino to carboxy orientation, respectively. Numeric ranges are inclusive of the numbers defining the range.

As used herein, the term "increased fiber length" or "fiber having an increased length" refers to cotton fibers in transgenic or infected plants that are at least 4% longer, preferably at least 5% longer, more preferably at least 6% longer and most preferably at least 7% longer than cotton fibers in non-transgenic or non-infected plants.

Thus in one aspect, the present invention provides an isolated nucleic acid encoding a GhWRIL protein comprising the amino acid sequence set forth in SEQ ID NO:2. In one embodiment, the nucleic acid comprises the nucleotide sequence set forth in SEQ ID NO:1. In another embodiment, the nucleic acid comprises the nucleotide sequence set forth as nucleotides 25-1338 of SEQ ID NO:1. In an additional embodiment, the nucleic acid comprises the nucleotide sequence set forth as nucleotides 25-1341 of SEQ ID NO:1. In a further embodiment, the nucleic acid further comprises a plant operable promoter operably linked to the nucleic acid. In one embodiment, the promoter is a seed specific promoter. In another embodiment, the seed specific promoter is a cotton seed specific promoter.

In a second aspect, the present invention provides an isolated nucleic acid encoding a GrWRIL protein comprising the amino acid sequence set forth in SEQ ID NO:4. In one embodiment, the nucleic acid comprises the nucleotide sequence set forth in SEQ ID NO:3. In another embodiment, the nucleic acid comprises the nucleotide sequence set forth as nucleotides 32-1345 of SEQ ID NO:3. In an additional embodiment, the nucleic acid comprises the nucleotide sequence set forth as nucleotides 32-1348 of SEQ ID NO:3. In a further embodiment, the nucleic acid further comprises a plant operable promoter operably linked to the nucleic acid. In one embodiment, the promoter is a seed specific promoter. In another embodiment, the seed specific promoter is a cotton seed specific promoter.

In a third aspect, the present invention provides a construct or vector comprising an isolated nucleic acid as described herein. In one embodiment, the construct or vector is an expression construct or vector. In another embodiment, the construct or vector further comprises a selectable marker.

In a further embodiment, the construct or vector comprises a Cre-lox recombination marker free system.

In a fourth aspect, the present invention provides a transgenic plant comprising a nucleic acid or vector described herein. In one embodiment, the transgenic plant is a cotton plant.

In a fifth aspect, the present invention provides for the down regulation of a cotton WRIL gene. In one embodiment, the down regulation of a cotton WRIL gene involves using RNA interference (RNAi), including microRNA and hairpin RNA. In another embodiment, the down regulation of a cotton WRIL gene involves using viral induced gene silencing (VIGS). In one embodiment, a nucleic acid is provided which down regulates the GhWRIL gene. In another embodiment, a nucleic acid is provided which down regulates the GrWRIL gene. In one embodiment, the nucleic acid further comprises a plant operable promoter operably linked to the nucleic acid. In one embodiment, the promoter is a seed specific promoter. In another embodiment, the seed specific promoter is a cotton seed promoter. According to one embodiment, the present invention also provides a vector comprising an isolated nucleic acid as described herein. In one embodiment, the vector is an expression vector. In another embodiment, the vector further comprises a selectable marker. In a further embodiment, the vector comprises a Cre-lox recombination marker free system. According to this aspect, the present invention further provides a transgenic or infected plant comprising a nucleic acid or vector described herein. In one embodiment, the transgenic or infected plant is a cotton plant.

According to this aspect, the nucleic acid is selected to inhibit expression of the native gene or to silence the native gene within a plant's tissues to achieve a desired phenotype. In one embodiment, expression of the native gene is inhibited. Such inhibition might be accomplished, for example, with transformation of a plant cell to comprise a promoter linked to an antisense nucleotide sequence, hairpin, RNA interfering molecule, double stranded RNA, microRNA or other nucleic acid molecule, such that tissue-preferred expression of the molecule interferes with translation of the mRNA of the native DNA sequence or otherwise inhibits expression of the native DNA sequence in plant cells. For further description of RNAi techniques or microRNA techniques, see, e.g., U.S. Pat. Nos. 5,034,323; 6,326,527; 6,452,067; 6,573,099; 6,753,139; and 6,777,588. See also International Publication Nos. WO 97/01952, WO 98/36083, WO 98/53083, WO 99/32619 and WO 01/75164; and U.S. Patent Application Publication Nos. 2003/0175965, 2003/0175783, 2003/0180945, 2004/0214330, 2005/0244858, 2005/0277610, 2006/0130176, 2007/0265220, 2008/0313773, 2009/0094711, 2009/0215860, 2009/0308041, 2010/0058498 and 2011/0091975. RNAi molecules or microRNA molecules can be prepared by the skilled artisan using techniques well known in the art, including techniques for the selection and testing of RNAi molecules and microRNA molecules that are useful for down regulating a cotton WRIL gene. In another embodiment, the native gene may be silenced by using VIGS. Such silencing may be accomplished by infecting a cotton plant a VIGS system that contains at least a partial fragment of a candidate gene to be silenced. For further description of a VIGS system useful for cotton, see International Publication No. WO 2010/144058.

The construct typically includes regulatory regions operatively linked to the 5' side of the nucleic acid described herein (such as a nucleic acid encoding a cotton WRIL protein or a nucleic acid encoding an RNAi molecule to down regulate a cotton WRIL gene) and/or to the 3' side of the nucleic acid. A cassette containing all of these elements is also referred to herein as an expression cassette. The expression cassettes may additionally contain 5' leader sequences in the expression cassette construct. The regulatory regions (i.e., promoters, transcriptional regulatory regions, and translational termination regions) and/or the polynucleotide encoding a signal anchor may be native/analogous to the host cell or to each other. The promoters and tissue-specific promoters, such as seed promoters and especially cotton seed promoters, are particularly useful for preparing constructs for the transformation of cotton. Alternatively, the regulatory regions and/or the polynucleotide encoding a signal anchor may be heterologous to the host cell or to each other. See, U.S. Pat. No. 7,205,453 and U.S. Patent Application Publication Nos. 2006/0218670, 2006/0248616 and 20090100536, and the references cited therein. The expression cassettes may additionally contain 5' leader sequences in the expression cassette construct. Such leader sequences can act to enhance translation. Translation leaders are known in the art and include those described in International Publication No. WO 2008/094127 and the references cited therein.

A number of promoters can be used in the practice of the invention. The promoters can be selected based on the desired outcome. That is, the nucleic acids can be combined with constitutive, tissue-preferred, or other promoters for expression in the host cell of interest. Such constitutive promoters include, for example, the core promoter of the Rsyn7 (WO 99/48338 and U.S. Pat. No. 6,072,050); the core CaMV 35S promoter (Odell et al., 1985); rice actin (McElroy et al., 1990); ubiquitin (Christensen and Quail, 1989; Christensen et al., 1992); pEMU (Last et al., 1991); MAS (Velten et al., 1984); ALS promoter (U.S. Pat. No. 5,659,026), and the like. Other constitutive promoters include, for example, those disclosed in U.S. Pat. Nos. 5,608,149; 5,608,144; 5,604,121; 5,569,597; 5,466,785; 5,399,680; 5,268,463; and 5,608,142.

Other promoters include inducible promoters, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. Other promoters include those that are expressed locally at or near the site of pathogen infection. In further embodiments, the promoter may be a wound-inducible promoter. In other embodiments, chemical-regulated promoters can be used to modulate the expression of a gene in a plant through the application of an exogenous chemical regulator. The promoter may be a chemical-inducible promoter, where application of the chemical induces gene expression, or a chemical-repressible promoter, where application of the chemical represses gene expression. In addition, tissue-preferred promoters can be utilized to target enhanced expression of a polynucleotide of interest within a particular plant tissue. Each of these promoters are described in U.S. Pat. Nos. 6,506,962, 6,575,814, 6,972,349 and 7,301,069 and in U.S. Patent Application Publication Nos. 2007/0061917 and 2007/0143880. Cotton seed promoters are well known to the skilled artisan and include, but are not limited to the Gh-sp promoter (Song et al., 2000) and the α-globulin B promoter (Sunilkumar et al., 2002). Any other recourse seed specific promoter can be used to, for example soybean 7S storage gene promoter (Qu et al., 2012), Jatropha oleosin promoter (Popluechai et al., 2011), 2S storage protein promoter, and the like.

Generally, the expression cassette may additionally comprise a selectable marker gene for the selection of transformed cells. Selectable marker genes are utilized for the selection of transformed cells or tissues. Usually, the plant selectable marker gene will encode antibiotic resistance, with suitable genes including at least one set of genes coding for resistance to the antibiotic spectinomycin, the strepto- mycin phosphotransferase (spt) gene coding for streptomy- cin resistance, the neomycin phosphotransferase (nptII) gene encoding kanamycin or geneticin resistance, the hygromycin phosphotransferase (hpt or aphiv) gene encoding resistance to hygromycin, acetolactate synthase (als) genes. Alterna- tively, the plant selectable marker gene will encode herbi- cide resistance such as resistance to the sulfonylurea-type herbicides, glufosinate, glyphosate, ammonium, bromoxy- nil, imidazolinones, and 2,4-dichlorophenoxyacetate (2,4- D), including genes coding for resistance to herbicides which act to inhibit the action of glutamine synthase such as phosphinothricin or basta (e.g., the bar gene). See generally, International Publication No. WO 02/36782, U.S. Pat. No. 7,205,453 and U.S. Patent Application Publication Nos. 2006/0218670, 2006/0248616, 2007/0143880 and 2009/ 0100536, and the references cited therein. See also, Jefferson et al. (1991); De Wet et al. (1987); Goff et al. (1990); Kain et al. (1995) and Chiu et al. (1996). This list of selectable marker genes is not meant to be limiting. Any selectable marker gene can be used. The selectable marker gene is also under control of a promoter operable in the plant species to be transformed. Such promoters include those described in International Publication No. WO 2008/094127 and the references cited therein.

Alternatively, the expression cassette may additionally comprise a Cre-lox recombination marker free system, such as described by Zuo et al. (2001). Such a system is useful for producing selection marker free transgenic cotton plants.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubsti- tutions, e.g. transitions and transversions may be involved.

Once a nucleic acid has been cloned into an expression vector, it may be introduced into a plant cell using conven- tional transformation procedures. The term "plant cell" is intended to encompass any cell derived from a plant includ- ing undifferentiated tissues such as callus and suspension cultures, as well as plant seeds, pollen or plant embryos. Plant tissues suitable for transformation include leaf tissues, root tissues, meristems, protoplasts, hypocotyls, cotyledons, scutellum, shoot apex, root, immature embryo, pollen, and anther. "Transformation" means the directed modification of the genome of a cell by the external application of recom- binant DNA from another cell of different genotype, leading to its uptake and integration into the subject cell's genome. In this manner, genetically modified plants, plant cells, plant tissue, seed, and the like can be obtained.

DNA constructs containing the promoters of the present invention can be used to transform any plant and particularly cotton plants. The constructs may be introduced into the genome of the desired plant host by a variety of conventional techniques. Techniques for transforming a wide variety of higher plant species are well known and described in the technical and scientific literature. Transformation protocols may vary depending on the type of plant or plant cell, i.e., monocot or dicot, targeted for transformation, as is well known to the skilled artisan. For example, the DNA con- struct may be introduced directly into the genomic DNA of the plant cell using techniques such as electroporation and microinjection of plant cell protoplasts, or the DNA con- structs can be introduced directly to plant tissue using ballistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. Thus, any method, which provides for effective transformation/transfection may be employed. See, for example, U.S. Pat. Nos. 7,241,937, 7,273,966 and 7,291,765 and U.S. Patent Application Publication Nos. 2007/0231905 and 2008/0010704 and references cited therein. See also, International Publication Nos. WO 2005/103271 and WO 2008/094127 and references cited therein. Techniques which have been used to transform oil palm include biolistic- mediated transformation and *Agrobacterium*-mediated transformation. See, for example, Masli et al. (2009); Omid- var et al. (2008); Parveez et al. (2008); Abdullah et al. (2005); Parveez et al. (2000); Chowdhury, et al. (1997); and U.S. Patent Application Publication No. 2009/0038032.

Transformed plant cells which are derived by any of the above transformation techniques can be cultured to regen- erate a whole plant which possesses the transformed geno- type and thus the desired phenotype, e.g., a transgenic plant. A "transgenic plant" is a plant into which foreign DNA has been introduced. A "transgenic plant" encompasses all descendants, hybrids, and crosses thereof, whether repro- duced sexually or asexually, and which continue to harbor the foreign DNA. Regeneration techniques rely on manipu- lation of certain phytohormones in a tissue culture growth medium, typically relying on a biocide and/or herbicide marker which has been introduced together with the desired nucleotide sequences. See for example, International Publi- cation No. WO 2008/094127 and references cited therein.

The foregoing methods for transformation are typically used for producing a transgenic variety in which the expres- sion cassette is stably incorporated. After the expression cassette is stably incorporated in transgenic plants, it can be transferred to other plants by sexual crossing. In one embodiment, the transgenic variety could then be crossed, with another (non-transformed or transformed) variety, in order to produce a new transgenic variety. Alternatively, a genetic trait which has been engineered into a particular cotton line using the foregoing transformation techniques could be moved into another line using traditional back- crossing techniques that are well known in the plant breed- ing arts. For example, a backcrossing approach could be used to move an engineered trait from a public, non-elite variety into an elite variety, or from a variety containing a foreign gene in its genome into a variety or varieties which do not contain that gene. As used herein, "crossing" can refer to a simple X by Y cross, or the process of backcrossing, depending on the context. Any of a number of standard breeding techniques can be used, depending upon the spe- cies to be crossed.

Once transgenic plants of this type are produced, the plants themselves can be cultivated in accordance with conventional procedures. Transgenic seeds can, of course, be recovered from the transgenic plants. These seeds can then be planted in the soil and cultivated using conventional procedures to produce transgenic plants. The cultivated transgenic plants will express the DNA of interest in a tissue-preferred or tissue-specific manner as described herein.

In a sixth aspect, the present invention provides methods of increasing cotton fiber length in cotton. In one embodiment, a method involves modulating the level of activity of an enzyme involved in a fatty acid biosynthesis in the host cotton cell or cotton plant. In one embodiment, the enzyme is acetyl-CoA carboxylase (ACCase). In another embodiment, the enzyme is β-ketoacyl-acyl carrier protein synthase I (KASI). In a further embodiment, the enzyme is enoyl-acyl carrier protein reductase (ENR). The level of activity can be reduced by reducing expression of the enzyme. In one embodiment, the modulation of the level of activity of an enzyme is a reduction in the activity of the enzyme. The level of activity of an enzyme can be reduced by using RNAi techniques described herein in which the enzyme is the target for the RNAi. Alternatively, the level of activity of an enzyme can be reduced using VIGS techniques as described herein in which at least a partial fragment of the target gene is used.

In another embodiment, a method involves the manipulation of transcription factors which can regulate an enzyme involved in fatty acid biosynthesis. In one embodiment, the transcription factor is a cotton WRIL protein. In another embodiment the cotton WRIL protein is a GhWRIL protein or a GrWRIL protein. In one embodiment, the manipulation of the transcription factor is a reduction in the expression. In one embodiment, the expression of the transcription factor can be reduced by using RNAi techniques described herein in which the transcription factor mRNA is the target for the RNAi. Alternatively, the level of activity of the transcription factor can be reduced using VIGS techniques as described herein in which at least a partial fragment of the target transcription factor gene is used.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning*, 2nd Ed. (Cold Spring Harbor Laboratory Press, Cold Spring Harbor, N.Y.); Sambrook and Russell, 2001, *Molecular Cloning*, 3rd Ed. (Cold Spring Harbor Laboratory Press, Cold Spring Harbor, N.Y.); Ausubel et al., 1992), *Current Protocols in Molecular Biology* (John Wiley & Sons, including periodic updates); Glover, 1985, *DNA Cloning* (IRL Press, Oxford); Russell, 1984, *Molecular biology of plants: a laboratory course manual* (Cold Spring Harbor Laboratory Press, Cold Spring Harbor, N.Y.); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, 1988, *Antibodies*, (Cold Spring Harbor Laboratory Press, Cold Spring Harbor, N.Y.); *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Fire et al., *RNA Interference Technology: From Basic Science to Drug Development*, Cambridge University Press, Cambridge, 2005; Schepers, *RNA Interference in, Practice*, Wiley-VCH, 2005; Engelke, *RNA Interference (RNAi): The Nuts & Bolts of siRNA Technology*, DNA Press, 2003; Gott, *RNA Interference, Editing, and Modification: Methods and Protocols* (*Methods in Molecular Biology*), Human Press, Totowa, N.J., 2004; Sohail, *Gene Silencing by RNA Interference: Technology and Application*, CRC, 2004.

EXAMPLES

The present invention is described by reference to the following Examples, which is offered by way of illustration and is not intended to limit the invention in any manner. Standard techniques well known in the art or the techniques specifically described below were utilized.

Example 1

Materials and Methods

Cotton seedlings: Cotton seeds were amplified and germinated in a greenhouse. Four to 14 day old seedlings carrying 2-3 true leaves were used for VIGS assays. Younger seedlings with only cotyledons can also be used for VIGS assays.

Synthetic TRV RNA1 Expression Vector and Synthetic TRV RNA2 Expression Vector: See International publication No. WO 2010/144058.

Gene cloning and VIGS vector cloning: Candidate genes were amplified by PCR from cDNA products of *Gossypium hirsutum* leaf samples, and cloned into the XbaI and BamHI sites of the synthetic vector psTRV2001. The primers used in cloning the genes are set forth in Table 1, which also includes reference to the sequence of the cloned gene.

TABLE 1

Gene Primers and Gene Sequences

| Gene | Primer Sequences (5'→3') | SEQ ID NO: | Cloned Gene |
|---|---|---|---|
| WRIL | F: GGTTTTCTAGAGGAGTTTCTAAGTATC | 19 | 543 bp, |
|  | R: CGTATGGATCCCATGGAGAGGGATTCCGGGACC | 20 |  |
| KASI | F: ATATATCTAGAGGCTTTGTTATGGGTGAAGGTGC | 21 | 537 bp |
|  | R: GTCATGGATCCTGCCACCACAGAGTTGTGTCCACC | 22 |  |
| KASII | F: AATAATCTAGAGAGGATCTCATACAGGAAGATG | 23 | 510 bp |
|  | R: ATGCTGGATCCACACCAGCGTGAGCCAAGGCC | 24 |  |

TABLE 1-continued

Gene Primers and Gene Sequences

| Gene | Primer Sequences (5'→3') | SEQ ID NO: | Cloned Gene |
|---|---|---|---|
| ACCASE1 | F: ATAATTCTAGAGCATACAGAGACTCGATCAACC | 25 | 655 bp |
|  | R: TTGAAAGGATCCCCCTCAAAAAGATCCCTTTGCCCA | 26 |  |

Agrobacterium infiltration: Synthetic psTRV vectors and their derivatives were introduced into Agrobacterium strain AGL1 by electroporation. A 3 ml culture was grown for 24 hr at 28° C. in 50 mg/L kanamycin and 25 mg/L rifampicin. On the following day, the culture was inoculated into LB medium containing 50 mg/L kanamycin, 10 mM 2-(N-morpholino)ethanesulfonic acid (MES) and 20 µM acetosyringone and grown overnight in a 28° C. shaker. Agrobacterial cells were collected by centrifugation and resuspended in MMA solution (10 mM MES, 10 mM $MgCl_2$, 200 µM acetosyringone) to a final $OD_{600}$ of 1.5. The agrobacterial suspension was left at room temperature for 3-4 hr without shaking. Before infiltration, Agrobacterium culture containing the pTRV1/psTRV1 or pTRV2/psTRV2 vectors was mixed in a 1:1 ratio. Cotton plants were infiltrated with cultures either by syringe infiltration or by vacuum infiltration. For syringe infiltration, agrobacterial-inocula were delivered into the underside of two or three youngest fully-expanded leaf using a 1 ml needleless syringe. For vacuum infiltration, whole plants were submerged into agrobacterial-inocula and subjected to 80-90 kPa vacuum for 5 min, and then quickly releasing the vacuum, letting the inoculum rapidly enter plant tissues. All data described below were obtained by vacuum infiltration. However, syringe infiltration can also be used, but it is more time costly than vacuum infiltration. The silencing effect obtained with vacuum infiltration is better than that obtained with syringe infiltration. After infiltration, excess agrobacterial cell suspension was used to drench the root system of infiltrated plants. Infiltrated plants were grown in a growth chamber at 25° C. with 16 hr light/8 hr dark photoperiod cycle. The same method was also used in experiments testing VIGS in putative host plants.

Fatty Acid Analysis: Total lipid was extracted from 100 mg fresh cotton leaves or seeds as previously described (Ye et al., 2009). The outer seed coat was removed from dried cotton seeds. The remaining part was ground to fine powder and the lipids were extracted with hexane 3 times. The combined supernatant was transferred to a glass vial and the hexane was evaporated with a flow of dry nitrogen gas at 50° C. The weight of the raw oil was determined and the oil content was recorded as the ratio of raw oil to dried endosperm weight.

About 10 mg of lipid was transmethylated with 3N methanolic-HCl (SIGMA, MO, USA) plus 400 µL 2,2, Dimethoxypropane (SIGMA, MO, USA). The resultant FAMEs were separated by GC and detected using GC Agilent 6890 (Agilent, CA, USA) employing helium as the carrier gas and DB-23 columns for components separation. The GC analysis was performed at 140° C. for 50 sec and 30° C. $min^{-1}$ ramp to 240° C., and the final temperature was maintained for 50 sec. Peaks were identified based on their retention times compared with a FAME reference mixture (SIGMA, MO, USA). The fatty acid composition value included in the analyses was calculated based on the peak area percentage of total fatty acids in three biological replicates. The data were presented as mean±standard deviation.

RNA Extraction and Analysis: 100 mg leaf tissues or seeds were ground to fine powder in liquid $N_2$ and extracted with plant RNA purification reagent (Invitrogen, CA USA). RNA concentration was measured by Nanodrop (Thermo, DE, USA). M-MLV reverse transcriptase (Promega, WI, USA) was used for reverse transcription reactions and cDNAs production. The cDNAs were used to amplify corresponding genes coding region. Real-time PCR was performed with Power SYBR® Green PCR Master mix (Applied Biosystems, CA, USA) and run in ABI7900HT. All samples were run in triplicates and the data was analyzed with RQ manager at a pre-set Ct value (Applied Biosystems, CA, USA). Cotton UBQ14 transcript served as an internal control for RNA samples (F: CAACGCTCCATCTTGTCCTT (SEQ ID NO:27), R: TGATCGTCTTTCCCGTA AGC (SEQ ID NO:28)). Ct values included in the analyses were based on three biological replicates, with three technical replicates for each biological sample. Standard deviation was calculated based on the three biological replicates.

Example 2

Identification of Cotton WRI1-Like Gene Coding Sequence

A putative WRI1-like gene coding sequence was firstly identified with a database searching in GenBank with the reference of Arabidopsis WRI1 protein sequence (GenBank Accession number: AAP80382). Primers were designed as F: GGCACGAGGGGGGAAGAAAA AAAA (SEQ ID NO:29), R: TAACCCGAAACATCAACCATTA (SEQ ID NO:30) and PCR were performed with the cDNA of upland cotton to clone the full length cDNA, following with vector cloning and sequencing. The nucleotide sequence for the cDNA is set forth in SEQ ID NO:1. The deduced amino acid sequence is set forth in SEQ ID NO:2.

Figure 1A:
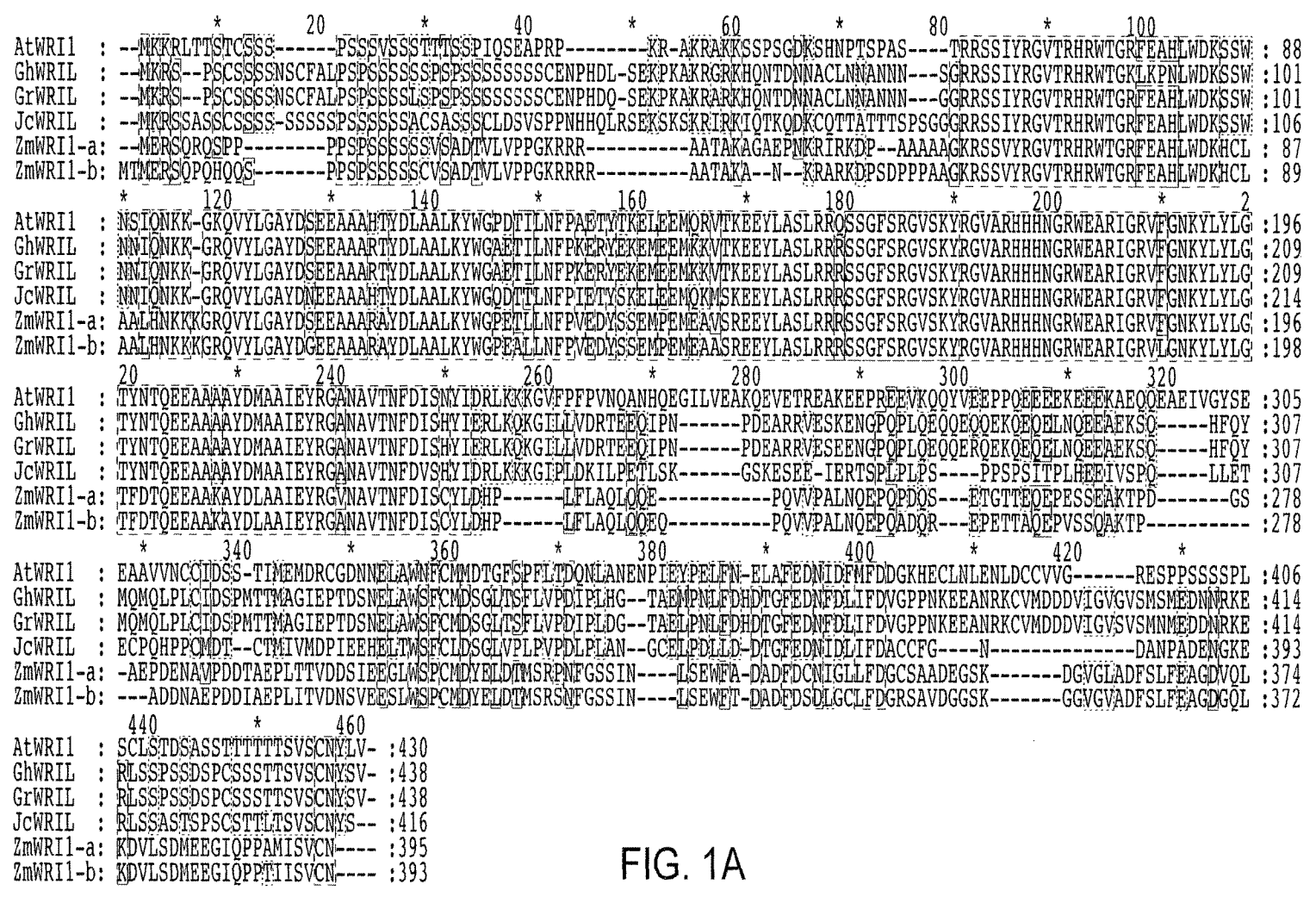

Another cotton WRIL protein was further identified from the EST database of Gossypium raimondii http://compbio.dfci.harvard.edu/tgi/plant.html. Wild cotton Gossypium raimondii is believed as one of the putative progenitor species of tetraploid cotton. The cDNA sequence for. GrWRIL is set forth in SEQ ID NO:3, and the deduced amino acid sequence is set forth as SEQ ID NO:4. Protein alignment and phylogenetic analysis were performed (FIGS. 1A and 1B). Base on the above data, cotton WRI1-like protein (GhWRIL) shares 51.4% identity with Arabidopsis WRI1 (AtWRI1). However, WRIL homologs from different cotton species shared 96.3% identity, which indicated the protein play a very important role on evolution of cotton species.

Example 3

Longer Fiber Length by Knock Down the Expression of GhWRIL

We were interested in the functional analysis of the role of WRIL on cotton fiber length. To amplify the WRIL from

*G. hirsutum*, PCR primers (SEQ ID NOs:19 and 20) were designed to amplify a 543-bp cDNA of *G. hirsutum* by PCR, and the GhWRIL fragment (SEQ ID NO:1) was inserted into the sTRV2 MCS site to give psTRV2:GhWRIL. The sequence of GhWRIL was also verified by sequencing. Cultures of *Agrobacterium* carrying psTRV 1 was mixed with cultures of *Agrobacterium* carrying either psTRV2: GhWRIL or vector control. The mixed culture was vacuum-infiltrated into *G. hirsutum* plants with 2-3 true leaves (for details see Example 1). There are no obvious phenotypes in vegetative organs of GhWRIL-silenced cotton plants, such as leaf width and pattern of trichome branching.

After cotton bolls matured and cotton fiber exposed out, bigger boll size and longer fiber length can be observed on GhWRIL-silenced cotton plants (FIG. 2). Cotton fiber was 29.2 mm in GhWRIL-silenced cotton plants while 27.3 mm in sTRV vector treated control cotton plants (FIG. 3). The seeds of GhWRIL-silenced cotton plants showed slimmer phenotypes compared with control seeds (FIG. 2). Furthermore, both seed weight and oil content reduced in GhWRIL-silenced cotton seed (FIG. 4). Fatty acid profile was also found to change to have lower oleate (18:1) and higher amount of linoleate (FIG. 5).

We next tried to identified the putative down-stream genes which are regulated by transcription factors WRIL in cotton seed. We performed quantitative realtime PCR, using total RNA extracted from seeds of treated plants to confirm the VIGS of the WRIL gene at the molecular and the results are shown in FIG. 6. WRIL RNA accumulation in the seeds of GhWRIL-silenced plant was much lower than that of plants infected with the empty sTRV vector and there is 22% of GhWRIL RNA was left in GhWRIL-silenced plants. Among all fatty acid biosynthesis enzymes, ACCase controls a major point of the pathway and catalyzes the rate limited step for lipid biosynthesis. ACCase catalyzes the carboxylation of acetyl-CoA to malonyl-CoA, which is the first committed step in fatty acid bisynthesis. In the GhWRIL-silenced seeds, homo-Accase1 was dramatic reduced to only 12% of control seeds. Enoyl-acyl carrier protein reductase (ENR) and ketoacyl-acyl carrier protein synthase (KASI) are two key genes among the obviously downregulated genes. KASI encodes the main enzyme for fatty acid condensation reaction and ENR is the last enzyme in the fatty acid elongation cycle. By contrast, there were no obvious changes of transcript levels for other FAS genes like those encoding ketoacyl-ACP synthases II (KASII) and pyruvate dehydrogenase (PDH1) (FIG. 6).

These results indicated GhWRIL may function to bind promoters of these three genes (ACCase1, KASI and ENR) to regulate their expression. When we down-regulated the activity of GhWRIL, the expression of these three key genes for fatty acid biosynthesis were down-regulated and the carbon flow distribution to oil was inhibited and on the other hand, the sucrose related final product cotton fiber was enhanced.

Example 4

Silencing of ACCase1 and KASI, KASII Leads to Vegetative Growth Defects

Since we identified target genes regulated by GhWRIL, we further tested whether we can enhance fiber length by manipulating of these genes directly.

Cotton ACCASE1 and KASI, KASII genes were identified as the method for GhWRIL and gene fragments were inserted into psTRV2 vectors (FIG. 7 and FIGS. 8A and 8B).

A partial coding sequence for GhACCase1 is set forth in SEQ ID NO:9, and the deduced amino acid sequence is set forth in SEQ ID NO:10. A coding sequence for GhKASI is set forth in SEQ ID NO:12, and the deduced amino acid sequence is set forth in SEQ ID NO:13. A coding sequence for GhKASII is set forth in SEQ ID NO:15, and the deduced amino acid sequence is set forth in SEQ ID NO:16. Cultures of *Agrobacterium* carrying psTRV 1 was mixed with cultures of *Agrobacterium* carrying either psTRV2:GhACCase1, GhKASI, GhKASII or vector control. The mixed culture was vacuum-infiltrated into *G. hirsutum* plants with 2-3 true leaves (for details see Example 1).

All of these three silenced plants showed severe phenotypes on plant vegetative growth (FIGS. 9A-9D and FIGS. 10A-10E).

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

Abdullah, R. et al. (2005). Immature embryo: A useful tool for oil palm (*Elaeis guineensis* Jacq.) genetic transformation studies. *Electronic Journal of Biotechnology* [online] vol. 8, no. 1 [Apr. 15, 2005). Available from: http colon // www dot ejbiotechnology dot info/content/vol8/issue1/full/1/index.html.

Baulcombe, D. (2004). RNA silencing in plants. *Nature* 431:356-363.

Brigneti, G. et al. (2004). Virus-induced gene silencing in *Solanum* species. *Plant J* 39:264-272.

Burch-Smith, T. M. et al. (2004). Applications and advantages of virus-induced gene silencing for gene function studies in plants. *Plant J* 39:734-746.

Cernac, A. and Benning. C. (2004). WRINKLED1 encodes an AP2/EREB domain protein involved in the control of storage compound biosynthesis in *Arabidopsis*. *Plant J* 40:575-585.

Chiu, W. et al. (1996). Engineered GFP as a vital reporter in plants. *Current Biology* 6:325-330.

Chowdhury, M. K. U. et al. (1997). Evaluation of five promoters for use in transformation of oil palm (*Elaeis guineensis* Jacq.) *Plant Cell Reports* 16:277-281.

Christensen, A. H. and Quail, P. H. (1989). Sequence analysis and transcriptional regulation by heat shock of polyubiquitin transcripts from maize. *Plant Mol Biol* 12:619-632.

Christensen, A. H. et al. (1992). Maize polyubiquitin genes: structure, thermal perturbation of expression and transcript splicing, and promoter activity following transfer to protoplasts by electroporation. *Plant Mol Biol* 18:675-689.

De Wet, J. R. et al. (1987). Firefly luciferase gene: structure and expression in mammalian cells. *Mol Cell Biol* 7:725-737.

Goff, S. A. et al. (1990). Transactivation of anthocyanin biosynthetic genes following transfer of B regulatory genes into maize tissues. *EMBO J* 9:2517-2522.

Jefferson, R. A. et al. (1991). *Plant Molecular Biology Manual*, ed. Gelvin et al., Kluwer Academic Publishers, pp. 1-33.

Jiang, Y. et al. (2012), Guo W, Zhu H, Ruan Y L, Zhang T: Overexpression of GhSusA1 increases plant biomass and improves cotton fiber yield and quality. *Plant Biotechnol J* 10:301-312.

Kain, S. R. et al. (1995). Green fluorescent protein as a reporter of gene expression and protein localization. *Biotechniques* 19:650-655.

Last, D. I. et al. (1991). pEmu: an improved promoter for gene expression in cereal cells. *Theor Appl Genet* 81:581-588.

Lee, J. et al. (2010). Xyloglucan endotransglycosylase/hydrolase genes in cotton and their role in fiber elongation. *Planta* 232:1191-1205.

Li, X. B. et al. (2005). The cotton ACTIN1 gene is functionally expressed in fibers and participates in fiber elongation. *Plant Cell* 17:859-875.

Mash, D. I. A. et al. (2009). Transformation of oil palm using *Agrobacterium tumefaciens*. *J Oil Palm Res* 21:643-652.

McElroy, D. et al. (1990). Isolation of an efficient actin promoter for use in rice transformation. *Plant Cell* 2:163-171.

Odell, J. T. et al. (1985). Identification of DNA sequences required for activity of the cauliflower mosaic virus 35S promoter. *Nature* 313:810-812.

Omidvar, V. et al. (2008). A transient assay to evaluate the expression of polyhydroxybutyrate genes regulated by oil palm mesocarp-specific promoter. *Plant Cell Rep* 27:1451-1459.

Parveez, G. K. A. et al. (2000). Transgenic oil palm: production and projection. *Biochemical Society Transactions* 28:969-972.

Parveez, G. K. A. (2008). Biolistic mediated production of transgenic oil palm. *Methods Mol Biol* 477:301-320.

Popluechai, S., et al. (2011). *Jatropha curcas* oil body proteasome and oleosins: L-form JcOle3 as a potential phylogenetic marker. *Plant Physiol Biochem* 49: 352-356.

Qu, J. et al. (2012). Development of marker-free transgenic *Jatropha* plants with increased levels of seed oleic acid. *Biotechnol Biofuels* 5:10.

Ruan, Y. L. et al. (2003). Suppression of sucrose synthase gene expression represses cotton fiber cell initiation, elongation, and seed development. *Plant Cell* 15:952-964.

Ruiz, M. T. et al. (1998). Initiation and maintenance of virus-induced gene silencing. *Plant Cell* 10:937-946.

Seagull, R. W. (1990). The effects of microtubule and microfilament disrupting agents on crytoskeletal arrays and wall deposition in developing cotton fibers. *Protoplasma* 159:44-59.

Song, P. et al. (2000). Expression of two tissue-specific promoters in transgenic cotton plants. *J Cotton Sci* 4:217-223.

Sunilkumar, G. et al. (2002). Cotton alpha-globulin promoter: isolation and functional characterization in transgenic cotton, *Arabidopsis*, and tobacco. *Transgenic Res* 11:347-359.

Velten, J. et al. (1984). Isolation of a dual plant promoter fragment from the Ti plasmid of *Agrobacterium tumefaciens*. *EMBO J* 3:2723-2730.

Wang, H. Y. et al. (2009). Down-regulation of GhADF1 gene expression affects cotton fibre properties. *Plant Biotechnol J* 7:13-23.

Wang, J. et al. (2010). Overexpression of a profilin (GhPFN2) promotes the progression of developmental phases in cotton fibers. *Plant Cell Physiol* 51:1276-1290.

Ye, J. et al. (2009). Rapid analysis of *Jatropha curcas* gene functions by virus-induced gene silencing. *Plant Biotechnol J* 7:964-976.

Ye, J. et al. (2010). Virus induced gene silencing (VIGS) for functional analysis of genes in cotton. International publication No. WO 2010/144058.

Zuo, J. et al. (2001). Chemical-regulated, site-specific DNA excision in transgenic plants. *Nat Biotechnol* 19:157-161.

What is claimed is:

1. A cDNA encoding a protein (a) comprising the amino acid sequence of SEQ ID NO:2; or (b) comprising the amino acid sequence of SEQ ID NO:4.

2. The cDNA of claim 1 encoding protein (a), wherein the cDNA comprises the nucleotide sequence of SEQ ID NO:1, 25-1338 of SEQ ID NO:1 or 25-1341 of SEQ ID NO:1.

3. The cDNA of claim 1 encoding protein (b) wherein the cDNA comprises the nucleotide sequence of SEQ ID NO:3, 32-1345 of SEQ ID NO:3 or 32-1348 of SEQ ID NO:3.

4. A nucleic acid construct comprising a plant operable promoter operably linked to the cDNA of claim 1.

5. The nucleic acid construct of claim 4, wherein the promoter is a seed specific promoter.

6. A transgenic plant cell, plant or plant seed comprising the cDNA of claim 1 stably integrated into its genome.

7. The transgenic plant cell, plant or plant seed of claim 6, wherein the plant is cotton.

8. A transgenic plant cell, plant or plant seed comprising the nucleic acid construct of claim 4 stably integrated in its genome.

9. The transgenic plant cell, plant or plant seed of claim 8, wherein the plant is cotton.

10. The nucleic acid construct of claim 4, wherein the promoter is heterologous to the cDNA.

* * * * *

SEQUENCE LISTING

```
<160> NUMBER OF SEQ ID NOS: 30

<210> SEQ ID NO 1
<211> LENGTH: 1445
<212> TYPE: DNA
<213> ORGANISM: Gossypium hirsutum
<220> FEATURE:
<221> NAME/KEY: CDS
<222> LOCATION: (25)..(1341)
```

<400> SEQUENCE: 1

| | | |
|---|---|---|
| ggcacgaggg gggaagaaaa aaaa atg aag agg tca ccg agt tgt tct tct<br>                                       Met Lys Arg Ser Pro Ser Cys Ser Ser<br>                                       1                   5 | 51 |
| tct tct aat tca tgc ttt gca ttg cca tca cca tca tca tca tca<br>Ser Ser Asn Ser Cys Phe Ala Leu Pro Ser Pro Ser Ser Ser Ser<br>10                15                   20                 25 | 99 |
| tca ccg tca ccg tct tcg tca tca tca tct tca tgt gag aac cct<br>Ser Pro Ser Pro Ser Ser Ser Ser Ser Ser Ser Cys Glu Asn Pro<br>                30                   35                   40 | 147 |
| cat gat cta tca gag aaa ccc aag gct aaa agg ggt aga aag cat caa<br>His Asp Leu Ser Glu Lys Pro Lys Ala Lys Arg Gly Arg Lys His Gln<br>                    45                   50                   55 | 195 |
| aac act gat aat aat gct tgt ttg aac aat gct aac aac aat agc ggt<br>Asn Thr Asp Asn Asn Ala Cys Leu Asn Asn Ala Asn Asn Asn Ser Gly<br>         60                   65                   70 | 243 |
| aga agg agc tct att tac aga gga gtc acc agg cat aga tgg act gga<br>Arg Arg Ser Ser Ile Tyr Arg Gly Val Thr Arg His Arg Trp Thr Gly<br>75                   80                   85 | 291 |
| aaa ttg aag ccc aac ctt tgg gac aag agt tct tgg aat aat att cag<br>Lys Leu Lys Pro Asn Leu Trp Asp Lys Ser Ser Trp Asn Asn Ile Gln<br>90                   95                  100               105 | 339 |
| aac aag aaa gga aga caa gtt tat tta ggg gct tat gat agt gag gag<br>Asn Lys Lys Gly Arg Gln Val Tyr Leu Gly Ala Tyr Asp Ser Glu Glu<br>                    110                  115               120 | 387 |
| gca gcg gct cga acc tat gat cta gcg gct ctc aaa tat tgg ggg gcg<br>Ala Ala Ala Arg Thr Tyr Asp Leu Ala Ala Leu Lys Tyr Trp Gly Ala<br>                    125                  130               135 | 435 |
| gaa acg ata ctg aac ttc ccg aaa gaa aga tat gaa aaa gag atg gaa<br>Glu Thr Ile Leu Asn Phe Pro Lys Glu Arg Tyr Glu Lys Glu Met Glu<br>         140                   145                  150 | 483 |
| gaa atg aag aaa gtg aca aag gaa gag tac ttg gcg tct cta cga cgt<br>Glu Met Lys Lys Val Thr Lys Glu Glu Tyr Leu Ala Ser Leu Arg Arg<br>155                   160                  165 | 531 |
| cgc agc agt ggg ttt tct aga gga gtt tct aag tat cgt ggg gta gct<br>Arg Ser Ser Gly Phe Ser Arg Gly Val Ser Lys Tyr Arg Gly Val Ala<br>170                 175                  180               185 | 579 |
| agg cat cac cac aat ggg agg tgg gaa gcc cga att ggt cga gtt ttt<br>Arg His His His Asn Gly Arg Trp Glu Ala Arg Ile Gly Arg Val Phe<br>                    190                  195               200 | 627 |
| gga aac aaa tat ctc tat tta ggg acc tat aat aca caa gag gaa gca<br>Gly Asn Lys Tyr Leu Tyr Leu Gly Thr Tyr Asn Thr Gln Glu Glu Ala<br>                    205                  210               215 | 675 |
| gca gca gca tat gat atg gca gct ttg gag tat agg ggg gcc aat gcc<br>Ala Ala Ala Tyr Asp Met Ala Ala Leu Glu Tyr Arg Gly Ala Asn Ala<br>         220                   225                  230 | 723 |
| gtg acc aat ttc gat att agc cat tac att gaa cgc ttg aag cag aaa<br>Val Thr Asn Phe Asp Ile Ser His Tyr Ile Glu Arg Leu Lys Gln Lys<br>235                   240                  245 | 771 |
| gga att ttg tta gta gat cga acg gaa gaa caa att ccc aac ccc gat<br>Gly Ile Leu Leu Val Asp Arg Thr Glu Glu Gln Ile Pro Asn Pro Asp<br>250                   255                  260               265 | 819 |
| gaa gct cga cga gta gaa tcc aaa gaa aat gga cca cag ccg ctg cag<br>Glu Ala Arg Arg Val Glu Ser Lys Glu Asn Gly Pro Gln Pro Leu Gln<br>                    270                  275               280 | 867 |
| gag cag caa gaa cag cag gaa aaa cag gaa caa gaa ttg aac caa gaa<br>Glu Gln Gln Glu Gln Gln Glu Lys Gln Glu Gln Glu Leu Asn Gln Glu<br>                    285                  290               295 | 915 |
| gag gcc gaa aaa tct caa cat ttt caa tac atg caa atg cag ctt cct | 963 |

```
                                                                                    -continued Glu Ala Glu Lys Ser Gln His Phe Gln Tyr Met Gln Met Gln Leu Pro
            300                 305                 310 cta tgc att gat agt ccg atg aca aca atg gcc ggt att gag cct act    1011
Leu Cys Ile Asp Ser Pro Met Thr Thr Met Ala Gly Ile Glu Pro Thr
315                 320                 325 gat agt aat gaa cta gca tgg agt ttc tgc atg gat tcc ggg ttg aca    1059
Asp Ser Asn Glu Leu Ala Trp Ser Phe Cys Met Asp Ser Gly Leu Thr
330                 335                 340                 345 tcg ttt ttg gtc ccg gac atc cct ctc cat ggc acc gct gaa atg cca    1107
Ser Phe Leu Val Pro Asp Ile Pro Leu His Gly Thr Ala Glu Met Pro
                350                 355                 360 aac ttg ttt gat cat gat acg gga ttt gag gat aac ttc gac ttg ata    1155
Asn Leu Phe Asp His Asp Thr Gly Phe Glu Asp Asn Phe Asp Leu Ile
            365                 370                 375 ttc gac gta ggg ccg cct aac aaa gaa gag gct aat cgg aaa tgc gtg    1203
Phe Asp Val Gly Pro Pro Asn Lys Glu Glu Ala Asn Arg Lys Cys Val
        380                 385                 390 atg gat gat gat gtg att gga gtc ggt gtt tcc atg agc atg gaa gac    1251
Met Asp Asp Asp Val Ile Gly Val Gly Val Ser Met Ser Met Glu Asp
395                 400                 405 aat aat agg aag gag aga ttg tca tca ccg tct tca gac tct cca tgt    1299
Asn Asn Arg Lys Glu Arg Leu Ser Ser Pro Ser Ser Asp Ser Pro Cys
410                 415                 420                 425 tca tca tcg aca acc tcg gtt tct tgc aac tac tct gtt taa            1341
Ser Ser Ser Thr Thr Ser Val Ser Cys Asn Tyr Ser Val
                430                 435 tggttgatgt tcgggttaa gagtttctga taattcggag tttgttgttg gaaatatgtt    1401
gtggggtgga tggatgccaa agatttaaaa tatcaatgca tttt                   1445

<210> SEQ ID NO 2
<211> LENGTH: 438
<212> TYPE: PRT
<213> ORGANISM: Gossypium hirsutum

<400> SEQUENCE: 2

Met Lys Arg Ser Pro Ser Cys Ser Ser Ser Asn Ser Cys Phe Ala
1               5                   10                  15

Leu Pro Ser Pro Ser Ser Ser Ser Ser Pro Ser Ser Ser
            20                  25                  30

Ser Ser Ser Ser Ser Cys Glu Asn Pro His Asp Leu Ser Glu Lys Pro
        35                  40                  45

Lys Ala Lys Arg Gly Arg Lys His Gln Asn Thr Asp Asn Asn Ala Cys
    50                  55                  60

Leu Asn Asn Ala Asn Asn Ser Gly Arg Arg Ser Ser Ile Tyr Arg
65                  70                  75                  80

Gly Val Thr Arg His Arg Trp Thr Gly Lys Leu Lys Pro Asn Leu Trp
                85                  90                  95

Asp Lys Ser Ser Trp Asn Asn Ile Gln Asn Lys Lys Gly Arg Gln Val
            100                 105                 110

Tyr Leu Gly Ala Tyr Asp Ser Glu Glu Ala Ala Ala Arg Thr Tyr Asp
        115                 120                 125

Leu Ala Ala Leu Lys Tyr Trp Gly Ala Glu Thr Ile Leu Asn Phe Pro
    130                 135                 140

Lys Glu Arg Tyr Glu Lys Glu Met Glu Met Lys Lys Val Thr Lys
145                 150                 155                 160

Glu Glu Tyr Leu Ala Ser Leu Arg Arg Arg Ser Ser Gly Phe Ser Arg
                165                 170                 175
```

```
Gly Val Ser Lys Tyr Arg Gly Val Ala Arg His His His Asn Gly Arg
            180                 185                 190

Trp Glu Ala Arg Ile Gly Arg Val Phe Gly Asn Lys Tyr Leu Tyr Leu
            195                 200                 205

Gly Thr Tyr Asn Thr Gln Glu Glu Ala Ala Ala Tyr Asp Met Ala
            210                 215                 220

Ala Leu Glu Tyr Arg Gly Ala Asn Ala Val Thr Asn Phe Asp Ile Ser
225                 230                 235                 240

His Tyr Ile Glu Arg Leu Lys Gln Lys Gly Ile Leu Val Asp Arg
                245                 250                 255

Thr Glu Glu Gln Ile Pro Asn Pro Asp Glu Ala Arg Arg Val Glu Ser
            260                 265                 270

Lys Glu Asn Gly Pro Gln Pro Leu Gln Glu Gln Gln Glu Gln Glu
            275                 280                 285

Lys Gln Glu Gln Glu Leu Asn Gln Glu Glu Ala Glu Lys Ser Gln His
            290                 295                 300

Phe Gln Tyr Met Gln Met Gln Leu Pro Leu Cys Ile Asp Ser Pro Met
305                 310                 315                 320

Thr Thr Met Ala Gly Ile Glu Pro Thr Asp Ser Asn Glu Leu Ala Trp
                325                 330                 335

Ser Phe Cys Met Asp Ser Gly Leu Thr Ser Phe Leu Val Pro Asp Ile
                340                 345                 350

Pro Leu His Gly Thr Ala Glu Met Pro Asn Leu Phe Asp His Asp Thr
                355                 360                 365

Gly Phe Glu Asp Asn Phe Asp Leu Ile Phe Asp Val Gly Pro Pro Asn
            370                 375                 380

Lys Glu Ala Asn Arg Lys Cys Val Met Asp Asp Val Ile Gly
385                 390                 395                 400

Val Gly Val Ser Met Ser Met Glu Asp Asn Asn Arg Lys Glu Arg Leu
                405                 410                 415

Ser Ser Pro Ser Ser Asp Ser Pro Cys Ser Ser Ser Thr Thr Ser Val
            420                 425                 430

Ser Cys Asn Tyr Ser Val
            435

<210> SEQ ID NO 3
<211> LENGTH: 1528
<212> TYPE: DNA
<213> ORGANISM: Gossypium raimondii
<220> FEATURE:
<221> NAME/KEY: CDS
<222> LOCATION: (32)..(1348)

<400> SEQUENCE: 3
ttatatactt agtgggggga aagaaaaaca a atg aag agg tca ccg agc tgt        52
                                   Met Lys Arg Ser Pro Ser Cys
                                    1               5 tct tct tct tct aat tcc tgc ttt gca ttg cca tca cca tca tca tca    100
Ser Ser Ser Ser Asn Ser Cys Phe Ala Leu Pro Ser Pro Ser Ser Ser
        10                  15                  20 tca tta tca cca tca cca tct tca tca tca tca tca tct tca tgt gag    148
Ser Leu Ser Pro Ser Pro Ser Ser Ser Ser Ser Ser Ser Cys Glu
    25                  30                  35 aac cct cat gat caa tca gag aaa ccc aag gct aaa agg gct aga aaa    196
Asn Pro His Asp Gln Ser Glu Lys Pro Lys Ala Lys Arg Ala Arg Lys
40                  45                  50                  55
```

```
cat caa aac act gat aat aat gct tgt ttg aac aat gct aac aac aat      244
His Gln Asn Thr Asp Asn Asn Ala Cys Leu Asn Asn Ala Asn Asn Asn
             60                  65                  70 ggc ggt aga agg agc tct att tac aga gga gtc acc agg cat aga tgg      292
Gly Gly Arg Arg Ser Ser Ile Tyr Arg Gly Val Thr Arg His Arg Trp
         75                  80                  85 act ggg aga ttt gag gct cac ctt tgg gac aag agt tct tgg aat aat      340
Thr Gly Arg Phe Glu Ala His Leu Trp Asp Lys Ser Ser Trp Asn Asn
         90                  95                 100 att cag aac aag aaa gga aga caa gtt tat tta ggg gct tat gac agt      388
Ile Gln Asn Lys Lys Gly Arg Gln Val Tyr Leu Gly Ala Tyr Asp Ser
        105                 110                 115 gag gag gca gcg gct cga acc tat gat cta gcg gct ctc aaa tat tgg      436
Glu Glu Ala Ala Ala Arg Thr Tyr Asp Leu Ala Ala Leu Lys Tyr Trp
120                 125                 130                 135 ggg gcg gaa acg ata ctg aac ttt ccg aaa gaa aga tat gaa aaa gag      484
Gly Ala Glu Thr Ile Leu Asn Phe Pro Lys Glu Arg Tyr Glu Lys Glu
                140                 145                 150 atg gaa gaa atg aag aaa gtg aca aag gaa gag tac ttg gcg tct cta      532
Met Glu Glu Met Lys Lys Val Thr Lys Glu Glu Tyr Leu Ala Ser Leu
            155                 160                 165 cga cgt cgc agc agt ggg ttt tct aga gga gtt tct aag tat cgt ggg      580
Arg Arg Arg Ser Ser Gly Phe Ser Arg Gly Val Ser Lys Tyr Arg Gly
        170                 175                 180 gta gct agg cat cac cac aat ggg agg tgg gaa gcc cga att ggt cga      628
Val Ala Arg His His His Asn Gly Arg Trp Glu Ala Arg Ile Gly Arg
        185                 190                 195 gtt ttt gga aac aaa tat ctc tat tta ggg acc tat aat aca caa gag      676
Val Phe Gly Asn Lys Tyr Leu Tyr Leu Gly Thr Tyr Asn Thr Gln Glu
200                 205                 210                 215 gaa gca gca gca gca tat gat atg gca gca ttg gag tat agg ggg gcc      724
Glu Ala Ala Ala Ala Tyr Asp Met Ala Ala Leu Glu Tyr Arg Gly Ala
                220                 225                 230 aat gcc gtg acc aat ttc gat att agc cat tac att gaa cgc ttg aag      772
Asn Ala Val Thr Asn Phe Asp Ile Ser His Tyr Ile Glu Arg Leu Lys
            235                 240                 245 cag aaa gga att ttg tta gta gat cga acg gaa gaa caa att ccc aac      820
Gln Lys Gly Ile Leu Leu Val Asp Arg Thr Glu Glu Gln Ile Pro Asn
        250                 255                 260 ccc gat gaa gct cga cga gta gaa tcg gaa gaa aat gga cca cag ccg      868
Pro Asp Glu Ala Arg Arg Val Glu Ser Glu Glu Asn Gly Pro Gln Pro
        265                 270                 275 ctg cag gag cag caa gaa cgg cag gaa aaa cag gaa caa gaa ttg aac      916
Leu Gln Glu Gln Gln Glu Arg Gln Glu Lys Gln Glu Gln Glu Leu Asn
280                 285                 290                 295 caa gaa gag gcc gaa aaa tct caa cat ttt caa tac atg caa atg cag      964
Gln Glu Glu Ala Glu Lys Ser Gln His Phe Gln Tyr Met Gln Met Gln
                300                 305                 310 ctt cct cta tgc att gat agt ccg atg aca aca atg gcc ggt att gag     1012
Leu Pro Leu Cys Ile Asp Ser Pro Met Thr Thr Met Ala Gly Ile Glu
            315                 320                 325 cct act gat agt aat gaa cta gca tgg agt ttc tgc atg gat tcc gga     1060
Pro Thr Asp Ser Asn Glu Leu Ala Trp Ser Phe Cys Met Asp Ser Gly
        330                 335                 340 ttg aca tcg ttt ttg gtc ccg gac atc cct ctc gac gga acc gct gaa     1108
Leu Thr Ser Phe Leu Val Pro Asp Ile Pro Leu Asp Gly Thr Ala Glu
        345                 350                 355 ttg cca aac ttg ttt gat cat gat acg gga ttt gag gat aac ttc gac     1156
Leu Pro Asn Leu Phe Asp His Asp Thr Gly Phe Glu Asp Asn Phe Asp
360                 365                 370                 375
```

```
ttg ata ttc gac gta ggg ccg cct aac aaa gaa gag gct aat cgg aaa    1204
Leu Ile Phe Asp Val Gly Pro Pro Asn Lys Glu Glu Ala Asn Arg Lys
            380                 385                 390 tgc gtg atg gat gat gat gtg att gga gtc agt gtt tcc atg aac atg    1252
Cys Val Met Asp Asp Asp Val Ile Gly Val Ser Val Ser Met Asn Met
        395                 400                 405 gaa gac gat aat agg aag gag aga ttg tca tca ccg tct tca gac tct    1300
Glu Asp Asp Asn Arg Lys Glu Arg Leu Ser Ser Pro Ser Ser Asp Ser
    410                 415                 420 cca tgt tca tca tcg aca acc tcg gtt tct tgt aac tac tct gtt taa    1348
Pro Cys Ser Ser Ser Thr Thr Ser Val Ser Cys Asn Tyr Ser Val
425                 430                 435 tggttgatgt ttcgggttaa gagtttctga taattcggag tttgttgctg gaaatatgtt    1408
gtggggtgga tggatgccaa agatttaaaa tatctttggt ttttgttgtt tgttttttgtt    1468 gttttttaatg catttctttt tgtttaatta tattgaaaaa aggaaaagac ttaacctgtt    1528

<210> SEQ ID NO 4
<211> LENGTH: 438
<212> TYPE: PRT
<213> ORGANISM: Gossypium raimondii

<400> SEQUENCE: 4

Met Lys Arg Ser Pro Ser Cys Ser Ser Ser Asn Ser Cys Phe Ala
1               5                   10                  15

Leu Pro Ser Pro Ser Ser Ser Leu Ser Pro Ser Pro Ser Ser Ser
            20                  25                  30

Ser Ser Ser Ser Ser Cys Glu Asn Pro His Asp Gln Ser Glu Lys Pro
        35                  40                  45

Lys Ala Lys Arg Ala Arg Lys His Gln Asn Thr Asp Asn Asn Ala Cys
50                  55                  60

Leu Asn Ala Asn Asn Asn Gly Gly Arg Arg Ser Ser Ile Tyr Arg
65                  70                  75                  80

Gly Val Thr Arg His Arg Trp Thr Gly Arg Phe Glu Ala His Leu Trp
                85                  90                  95

Asp Lys Ser Ser Trp Asn Asn Ile Gln Asn Lys Lys Gly Arg Gln Val
            100                 105                 110

Tyr Leu Gly Ala Tyr Asp Ser Glu Glu Ala Ala Ala Arg Thr Tyr Asp
        115                 120                 125

Leu Ala Ala Leu Lys Tyr Trp Gly Ala Glu Thr Ile Leu Asn Phe Pro
130                 135                 140

Lys Glu Arg Tyr Glu Lys Glu Met Glu Glu Met Lys Lys Val Thr Lys
145                 150                 155                 160

Glu Glu Tyr Leu Ala Ser Leu Arg Arg Arg Ser Ser Gly Phe Ser Arg
                165                 170                 175

Gly Val Ser Lys Tyr Arg Gly Val Ala Arg His His His Asn Gly Arg
            180                 185                 190

Trp Glu Ala Arg Ile Gly Arg Val Phe Gly Asn Lys Tyr Leu Tyr Leu
        195                 200                 205

Gly Thr Tyr Asn Thr Gln Glu Glu Ala Ala Ala Tyr Asp Met Ala
210                 215                 220

Ala Leu Glu Tyr Arg Gly Ala Asn Ala Val Thr Asn Phe Asp Ile Ser
225                 230                 235                 240

His Tyr Ile Glu Arg Leu Lys Gln Lys Gly Ile Leu Leu Val Asp Arg
                245                 250                 255
```

```
Thr Glu Glu Gln Ile Pro Asn Pro Asp Glu Ala Arg Arg Val Glu Ser
                260                 265                 270

Glu Glu Asn Gly Pro Gln Pro Leu Gln Glu Gln Glu Arg Gln Glu
        275                 280                 285

Lys Gln Glu Gln Glu Leu Asn Gln Glu Glu Ala Glu Lys Ser Gln His
        290                 295                 300

Phe Gln Tyr Met Gln Met Gln Leu Pro Leu Cys Ile Asp Ser Pro Met
305                 310                 315                 320

Thr Thr Met Ala Gly Ile Glu Pro Thr Asp Ser Asn Glu Leu Ala Trp
                325                 330                 335

Ser Phe Cys Met Asp Ser Gly Leu Thr Ser Phe Leu Val Pro Asp Ile
                340                 345                 350

Pro Leu Asp Gly Thr Ala Glu Leu Pro Asn Leu Phe Asp His Asp Thr
                355                 360                 365

Gly Phe Glu Asp Asn Phe Asp Leu Ile Phe Asp Val Gly Pro Pro Asn
        370                 375                 380

Lys Glu Glu Ala Asn Arg Lys Cys Val Met Asp Asp Val Ile Gly
385                 390                 395                 400

Val Ser Val Ser Met Asn Met Glu Asp Asp Asn Arg Lys Glu Arg Leu
                405                 410                 415

Ser Ser Pro Ser Ser Asp Ser Pro Cys Ser Ser Ser Thr Thr Ser Val
                420                 425                 430

Ser Cys Asn Tyr Ser Val
        435

<210> SEQ ID NO 5
<211> LENGTH: 430
<212> TYPE: PRT
<213> ORGANISM: Arabidopsis thaliana

<400> SEQUENCE: 5

Met Lys Lys Arg Leu Thr Thr Ser Thr Cys Ser Ser Ser Pro Ser Ser
1               5                   10                  15

Ser Val Ser Ser Ser Thr Thr Thr Ser Ser Pro Ile Gln Ser Glu Ala
                20                  25                  30

Pro Arg Pro Lys Arg Ala Lys Arg Ala Lys Lys Ser Ser Pro Ser Gly
            35                  40                  45

Asp Lys Ser His Asn Pro Thr Ser Pro Ala Ser Thr Arg Arg Ser Ser
        50                  55                  60

Ile Tyr Arg Gly Val Thr Arg His Arg Trp Thr Gly Arg Phe Glu Ala
65                  70                  75                  80

His Leu Trp Asp Lys Ser Ser Trp Asn Ser Ile Gln Asn Lys Lys Gly
                85                  90                  95

Lys Gln Val Tyr Leu Gly Ala Tyr Asp Ser Glu Glu Ala Ala Ala His
            100                 105                 110

Thr Tyr Asp Leu Ala Ala Leu Lys Tyr Trp Gly Pro Asp Thr Ile Leu
        115                 120                 125

Asn Phe Pro Ala Glu Thr Tyr Thr Lys Glu Leu Glu Glu Met Gln Arg
    130                 135                 140

Val Thr Lys Glu Glu Tyr Leu Ala Ser Leu Arg Arg Gln Ser Ser Gly
145                 150                 155                 160

Phe Ser Arg Gly Val Ser Lys Tyr Arg Gly Val Ala Arg His His His
                165                 170                 175

Asn Gly Arg Trp Glu Ala Arg Ile Gly Arg Val Phe Gly Asn Lys Tyr
            180                 185                 190
```

```
Leu Tyr Leu Gly Thr Tyr Asn Thr Gln Glu Ala Ala Ala Ala Tyr
        195                 200                 205

Asp Met Ala Ala Ile Glu Tyr Arg Gly Ala Asn Ala Val Thr Asn Phe
210                 215                 220

Asp Ile Ser Asn Tyr Ile Asp Arg Leu Lys Lys Lys Gly Val Phe Pro
225                 230                 235                 240

Phe Pro Val Asn Gln Ala Asn His Gln Glu Gly Ile Leu Val Glu Ala
                245                 250                 255

Lys Gln Glu Val Glu Thr Arg Glu Ala Lys Glu Glu Pro Arg Glu Glu
                260                 265                 270

Val Lys Gln Gln Tyr Val Glu Pro Pro Gln Glu Glu Glu Lys
            275                 280                 285

Glu Glu Glu Lys Ala Glu Gln Gln Glu Ala Glu Ile Val Gly Tyr Ser
290                 295                 300

Glu Glu Ala Ala Val Val Asn Cys Cys Ile Asp Ser Ser Thr Ile Met
305                 310                 315                 320

Glu Met Asp Arg Cys Gly Asp Asn Asn Glu Leu Ala Trp Asn Phe Cys
                325                 330                 335

Met Met Asp Thr Gly Phe Ser Pro Phe Leu Thr Asp Gln Asn Leu Ala
                340                 345                 350

Asn Glu Asn Pro Ile Glu Tyr Pro Glu Leu Phe Asn Glu Leu Ala Phe
                355                 360                 365

Glu Asp Asn Ile Asp Phe Met Phe Asp Asp Gly Lys His Glu Cys Leu
370                 375                 380

Asn Leu Glu Asn Leu Asp Cys Cys Val Val Gly Arg Glu Ser Pro Pro
385                 390                 395                 400

Ser Ser Ser Ser Pro Leu Ser Cys Leu Ser Thr Asp Ser Ala Ser Ser
                405                 410                 415

Thr Thr Thr Thr Thr Thr Ser Val Ser Cys Asn Tyr Leu Val
                420                 425                 430

<210> SEQ ID NO 6
<211> LENGTH: 416
<212> TYPE: PRT
<213> ORGANISM: Jatropha curcas

<400> SEQUENCE: 6

Met Lys Arg Ser Ser Ala Ser Ser Cys Ser Ser Ser Ser Ser Ser Ser
1               5                   10                  15

Ser Ser Pro Ser Ser Ser Ser Ser Ala Cys Ser Ala Ser Ser Ser
            20                  25                  30

Cys Leu Asp Ser Val Ser Pro Pro Asn His His Gln Leu Arg Ser Glu
                35                  40                  45

Lys Ser Lys Ser Lys Arg Ile Arg Lys Ile Gln Thr Lys Gln Asp Lys
        50                  55                  60

Cys Gln Thr Thr Ala Thr Thr Thr Ser Pro Ser Gly Gly Gly Arg Arg
65                  70                  75                  80

Ser Ser Ile Tyr Arg Gly Val Thr Arg His Arg Trp Thr Gly Arg Phe
                85                  90                  95

Glu Ala His Leu Trp Asp Lys Ser Ser Trp Asn Ile Gln Asn Lys
            100                 105                 110

Lys Gly Arg Gln Val Tyr Leu Gly Ala Tyr Asp Asn Glu Glu Ala Ala
        115                 120                 125

Ala His Thr Tyr Asp Leu Ala Ala Leu Lys Tyr Trp Gly Gln Asp Thr
```

130                 135                 140
Thr Leu Asn Phe Pro Ile Glu Thr Tyr Ser Lys Glu Leu Glu Met
145                 150                 155                 160

Gln Lys Met Ser Lys Glu Glu Tyr Leu Ala Ser Leu Arg Arg Arg Ser
                165                 170                 175

Ser Gly Phe Ser Arg Gly Val Ser Lys Tyr Arg Gly Val Ala Arg His
                180                 185                 190

His His Asn Gly Arg Trp Glu Ala Arg Ile Gly Arg Val Phe Gly Asn
                195                 200                 205

Lys Tyr Leu Tyr Leu Gly Thr Tyr Asn Thr Gln Glu Glu Ala Ala Ala
                210                 215                 220

Tyr Asp Met Ala Ala Ile Glu Tyr Arg Gly Ala Asn Ala Val Thr Asn
225                 230                 235                 240

Phe Asp Val Ser His Tyr Ile Asp Arg Leu Lys Lys Gly Ile Pro
                245                 250                 255

Leu Asp Lys Ile Leu Pro Glu Thr Leu Ser Lys Gly Ser Lys Glu Ser
                260                 265                 270

Glu Glu Ile Glu Arg Thr Ser Pro Leu Pro Leu Pro Ser Pro Ser
                275                 280                 285

Pro Ser Ile Thr Pro Leu His Glu Glu Ile Val Ser Pro Gln Leu Leu
                290                 295                 300

Glu Thr Glu Cys Pro Gln His Pro Pro Cys Met Asp Thr Cys Thr Met
305                 310                 315                 320

Ile Val Met Asp Pro Ile Glu Glu His Glu Leu Thr Trp Ser Phe Cys
                325                 330                 335

Leu Asp Ser Gly Leu Val Pro Leu Pro Val Pro Asp Leu Pro Leu Ala
                340                 345                 350

Asn Gly Cys Glu Leu Pro Asp Leu Leu Asp Asp Thr Gly Phe Glu Asp
                355                 360                 365

Asn Ile Asp Leu Ile Phe Asp Ala Cys Cys Phe Gly Asn Asp Ala Asn
                370                 375                 380

Pro Ala Asp Glu Asn Gly Lys Glu Arg Leu Ser Ser Ala Ser Thr Ser
385                 390                 395                 400

Pro Ser Cys Ser Thr Thr Leu Thr Ser Val Ser Cys Asn Tyr Ser Val
                405                 410                 415

<210> SEQ ID NO 7
<211> LENGTH: 395
<212> TYPE: PRT
<213> ORGANISM: Zea mays

<400> SEQUENCE: 7

Met Glu Arg Ser Gln Arg Gln Ser Pro Pro Pro Ser Pro Ser Ser
1               5                   10                  15

Ser Ser Ser Ser Val Ser Ala Asp Thr Val Leu Val Pro Pro Gly Lys
                20                  25                  30

Arg Arg Arg Ala Ala Thr Ala Lys Ala Gly Ala Glu Pro Asn Lys Arg
                35                  40                  45

Ile Arg Lys Asp Pro Ala Ala Ala Ala Gly Lys Arg Ser Ser Val
50                  55                  60

Tyr Arg Gly Val Thr Arg His Arg Trp Thr Gly Arg Phe Glu Ala His
65                  70                  75                  80

Leu Trp Asp Lys His Cys Leu Ala Ala Leu His Asn Lys Lys Lys Gly
                85                  90                  95

-continued

```
Arg Gln Val Tyr Leu Gly Ala Tyr Asp Ser Glu Ala Ala Ala Arg
            100                 105                 110
Ala Tyr Asp Leu Ala Ala Leu Lys Tyr Trp Gly Pro Glu Thr Leu Leu
        115                 120                 125
Asn Phe Pro Val Glu Asp Tyr Ser Ser Glu Met Pro Glu Met Glu Ala
    130                 135                 140
Val Ser Arg Glu Glu Tyr Leu Ala Ser Leu Arg Arg Arg Ser Ser Gly
145                 150                 155                 160
Phe Ser Arg Gly Val Ser Lys Tyr Arg Gly Val Ala Arg His His His
                165                 170                 175
Asn Gly Arg Trp Glu Ala Arg Ile Gly Arg Val Phe Gly Asn Lys Tyr
            180                 185                 190
Leu Tyr Leu Gly Thr Phe Asp Thr Gln Glu Glu Ala Ala Lys Ala Tyr
        195                 200                 205
Asp Leu Ala Ala Ile Glu Tyr Arg Gly Val Asn Ala Val Thr Asn Phe
    210                 215                 220
Asp Ile Ser Cys Tyr Leu Asp His Pro Leu Phe Leu Ala Gln Leu Gln
225                 230                 235                 240
Gln Glu Pro Gln Val Val Pro Ala Leu Asn Gln Glu Pro Gln Pro Asp
                245                 250                 255
Gln Ser Glu Thr Gly Thr Thr Glu Gln Glu Pro Glu Ser Ser Glu Ala
            260                 265                 270
Lys Thr Pro Asp Gly Ser Ala Glu Pro Asp Glu Asn Ala Val Pro Asp
        275                 280                 285
Asp Thr Ala Glu Pro Leu Ser Thr Val Asp Asp Ser Ile Glu Glu Gly
    290                 295                 300
Leu Trp Ser Pro Cys Met Asp Tyr Glu Leu Asp Thr Met Ser Arg Pro
305                 310                 315                 320
Asn Phe Gly Ser Ser Ile Asn Leu Ser Glu Trp Phe Ala Asp Ala Asp
                325                 330                 335
Phe Asp Cys Asn Ile Gly Cys Leu Phe Asp Gly Cys Ser Ala Ala Asp
            340                 345                 350
Glu Gly Ser Lys Asp Gly Val Gly Leu Ala Asp Phe Ser Leu Phe Glu
        355                 360                 365
Ala Gly Asp Val Gln Leu Lys Asp Val Leu Ser Asp Met Glu Glu Gly
    370                 375                 380
Ile Gln Pro Pro Ala Met Ile Ser Val Cys Asn
385                 390                 395

<210> SEQ ID NO 8
<211> LENGTH: 393
<212> TYPE: PRT
<213> ORGANISM: Zea mays

<400> SEQUENCE: 8

Met Thr Met Glu Arg Ser Gln Pro Gln His Gln Gln Ser Pro Pro Ser
1               5                   10                  15
Pro Ser Ser Ser Ser Cys Val Ser Ala Asp Thr Val Leu Val Pro
                20                  25                  30
Pro Gly Lys Arg Arg Arg Ala Ala Thr Ala Lys Ala Asn Lys Arg
        35                  40                  45
Ala Arg Lys Asp Pro Ser Asp Pro Pro Ala Ala Gly Lys Arg Ser
    50                  55                  60
Ser Val Tyr Arg Gly Val Thr Arg His Arg Trp Thr Gly Arg Phe Glu
65                  70                  75                  80
```

```
Ala His Leu Trp Asp Lys His Cys Leu Ala Ala Leu His Asn Lys Lys
             85                  90                  95

Lys Gly Arg Gln Val Tyr Leu Gly Ala Tyr Asp Gly Glu Glu Ala Ala
            100                 105                 110

Ala Arg Ala Tyr Asp Leu Ala Ala Leu Lys Tyr Trp Gly Pro Glu Ala
        115                 120                 125

Leu Leu Asn Phe Pro Val Glu Asp Tyr Ser Ser Glu Met Pro Glu Met
        130                 135                 140

Glu Ala Ala Ser Arg Glu Glu Tyr Leu Ala Ser Leu Arg Arg Arg Ser
145                 150                 155                 160

Ser Gly Phe Ser Arg Gly Val Ser Lys Tyr Arg Gly Val Ala Arg His
                165                 170                 175

His His Asn Gly Arg Trp Glu Ala Arg Ile Gly Arg Val Leu Gly Asn
            180                 185                 190

Lys Tyr Leu Tyr Leu Gly Thr Phe Asp Thr Gln Glu Glu Ala Ala Lys
        195                 200                 205

Ala Tyr Asp Leu Ala Ala Ile Glu Tyr Arg Gly Ala Asn Ala Val Thr
    210                 215                 220

Asn Phe Asp Ile Ser Cys Tyr Leu Asp His Pro Leu Phe Leu Ala Gln
225                 230                 235                 240

Leu Gln Gln Glu Gln Pro Gln Val Val Pro Ala Leu Asp Gln Glu Pro
                245                 250                 255

Gln Ala Asp Gln Arg Glu Pro Glu Thr Thr Ala Gln Glu Pro Val Ser
            260                 265                 270

Ser Gln Ala Lys Thr Pro Ala Asp Asp Asn Ala Glu Pro Asp Asp Ile
        275                 280                 285

Ala Glu Pro Leu Ile Thr Val Asp Asn Ser Val Glu Glu Ser Leu Trp
    290                 295                 300

Ser Pro Cys Met Asp Tyr Glu Leu Asp Thr Met Ser Arg Ser Asn Phe
305                 310                 315                 320

Gly Ser Ser Ile Asn Leu Ser Glu Trp Phe Thr Asp Ala Asp Phe Asp
                325                 330                 335

Ser Asp Leu Gly Cys Leu Phe Asp Gly Arg Ser Ala Val Asp Gly Gly
            340                 345                 350

Ser Lys Gly Gly Val Gly Val Ala Asp Phe Ser Leu Phe Glu Ala Gly
        355                 360                 365

Asp Gly Gln Leu Lys Asp Val Leu Ser Asp Met Glu Glu Gly Ile Gln
    370                 375                 380

Pro Pro Thr Ile Ile Ser Val Cys Asn
385                 390

<210> SEQ ID NO 9
<211> LENGTH: 2579
<212> TYPE: DNA
<213> ORGANISM: Gossypium hirsutum
<220> FEATURE:
<221> NAME/KEY: CDS
<222> LOCATION: (3)..(1946)

<400> SEQUENCE: 9 gt tct ttt ggc cca aga gag gat gca ttc ttc ctt gct gta act gat     47
   Ser Phe Gly Pro Arg Glu Asp Ala Phe Phe Leu Ala Val Thr Asp
   1               5                  10                  15 ctt gcc tgc agt aag aaa ctg cct tta att tat ttg gct gct aac tct    95
Leu Ala Cys Ser Lys Lys Leu Pro Leu Ile Tyr Leu Ala Ala Asn Ser
            20                  25                  30
```

| | | | | | | | | | | | | | | | | |
|---|---|---|---|---|---|---|---|---|---|---|---|---|---|---|---|---|
| ggt | gcc | cgt | att | ggg | gta | gct | gaa | gaa | gtc | aaa | gct | tgt | ttt | aaa | gtt | 143 |
| Gly | Ala | Arg | Ile | Gly | Val | Ala | Glu | Glu | Val | Lys | Ala | Cys | Phe | Lys | Val | |
| | | | 35 | | | | 40 | | | | 45 | | | | | |
| ggt | tgg | tct | aat | gaa | tcc | agc | cct | gag | cgt | ggt | ttt | cag | tat | gtc | tac | 191 |
| Gly | Trp | Ser | Asn | Glu | Ser | Ser | Pro | Glu | Arg | Gly | Phe | Gln | Tyr | Val | Tyr | |
| | 50 | | | | | 55 | | | | | 60 | | | | | |
| tta | act | cct | gag | gat | tat | act | aag | att | gga | tca | tca | gtc | att | gca | cat | 239 |
| Leu | Thr | Pro | Glu | Asp | Tyr | Thr | Lys | Ile | Gly | Ser | Ser | Val | Ile | Ala | His | |
| 65 | | | | | 70 | | | | | 75 | | | | | | |
| gag | atg | aag | ctg | gcc | agt | gga | gag | agc | aga | tgg | gtg | ata | gat | acc | att | 287 |
| Glu | Met | Lys | Leu | Ala | Ser | Gly | Glu | Ser | Arg | Trp | Val | Ile | Asp | Thr | Ile | |
| 80 | | | | 85 | | | | | 90 | | | | | 95 | | |
| gtt | ggg | aaa | gag | gat | ggt | ttg | gga | gtt | gag | aac | tta | act | ggt | agt | ggg | 335 |
| Val | Gly | Lys | Glu | Asp | Gly | Leu | Gly | Val | Glu | Asn | Leu | Thr | Gly | Ser | Gly | |
| | | | | 100 | | | | | 105 | | | | | 110 | | |
| gcc | att | gct | ggt | gca | tac | tct | cgg | gca | tac | aag | gaa | acc | ttt | acc | cta | 383 |
| Ala | Ile | Ala | Gly | Ala | Tyr | Ser | Arg | Ala | Tyr | Lys | Glu | Thr | Phe | Thr | Leu | |
| | | 115 | | | | | 120 | | | | | 125 | | | | |
| aca | tat | gtg | act | ggt | aga | act | gtg | gga | att | ggt | gct | tat | ctt | gct | cgt | 431 |
| Thr | Tyr | Val | Thr | Gly | Arg | Thr | Val | Gly | Ile | Gly | Ala | Tyr | Leu | Ala | Arg | |
| | 130 | | | | | 135 | | | | | 140 | | | | | |
| ctt | ggc | atg | cgg | tgc | ata | cag | aga | ctc | gat | caa | ccc | att | att | ttg | act | 479 |
| Leu | Gly | Met | Arg | Cys | Ile | Gln | Arg | Leu | Asp | Gln | Pro | Ile | Ile | Leu | Thr | |
| 145 | | | | | 150 | | | | | 155 | | | | | | |
| ggt | ttc | tca | gca | ttg | aac | aaa | ctt | cta | ggt | cgt | gag | gtg | tac | agc | tcc | 527 |
| Gly | Phe | Ser | Ala | Leu | Asn | Lys | Leu | Leu | Gly | Arg | Glu | Val | Tyr | Ser | Ser | |
| 160 | | | | | 165 | | | | | 170 | | | | | 175 | |
| cac | atg | caa | ctt | ggt | gga | cct | aaa | atc | atg | gca | aca | aat | ggt | gtt | gtc | 575 |
| His | Met | Gln | Leu | Gly | Gly | Pro | Lys | Ile | Met | Ala | Thr | Asn | Gly | Val | Val | |
| | | | 180 | | | | | 185 | | | | | 190 | | | |
| cat | ctc | acc | gtt | tcg | gat | gat | ctt | gaa | ggg | gtg | tca | gcc | ata | ttg | aac | 623 |
| His | Leu | Thr | Val | Ser | Asp | Asp | Leu | Glu | Gly | Val | Ser | Ala | Ile | Leu | Asn | |
| | | 195 | | | | | 200 | | | | | 205 | | | | |
| tgg | cta | agt | tgc | att | cct | cct | cat | ata | ggt | ggt | cca | ctt | ccc | att | tta | 671 |
| Trp | Leu | Ser | Cys | Ile | Pro | Pro | His | Ile | Gly | Gly | Pro | Leu | Pro | Ile | Leu | |
| | 210 | | | | | 215 | | | | | 220 | | | | | |
| aat | cca | tca | gat | cct | cca | gaa | agg | ctt | gtg | gag | tac | tta | cct | gaa | aat | 719 |
| Asn | Pro | Ser | Asp | Pro | Pro | Glu | Arg | Leu | Val | Glu | Tyr | Leu | Pro | Glu | Asn | |
| 225 | | | | | 230 | | | | | 235 | | | | | | |
| tcg | tgt | gat | cct | cgg | gcc | gca | att | tct | ggt | gct | tta | gat | agt | agt | ggc | 767 |
| Ser | Cys | Asp | Pro | Arg | Ala | Ala | Ile | Ser | Gly | Ala | Leu | Asp | Ser | Ser | Gly | |
| 240 | | | | | 245 | | | | | 250 | | | | | 255 | |
| aac | tgg | aag | gga | ggt | att | ttt | gac | agg | gat | agc | ttt | gtg | gag | acg | ctt | 815 |
| Asn | Trp | Lys | Gly | Gly | Ile | Phe | Asp | Arg | Asp | Ser | Phe | Val | Glu | Thr | Leu | |
| | | | | 260 | | | | | 265 | | | | | 270 | | |
| gaa | ggt | tgg | gct | aga | aca | gtt | gtg | aca | gga | agg | gca | aag | ctt | gga | gga | 863 |
| Glu | Gly | Trp | Ala | Arg | Thr | Val | Val | Thr | Gly | Arg | Ala | Lys | Leu | Gly | Gly | |
| | | | 275 | | | | | 280 | | | | | 285 | | | |
| atc | cct | gta | gga | ata | gtt | gca | gtt | gag | aca | cag | acg | gtg | atg | cag | gtt | 911 |
| Ile | Pro | Val | Gly | Ile | Val | Ala | Val | Glu | Thr | Gln | Thr | Val | Met | Gln | Val | |
| | | 290 | | | | | 295 | | | | | 300 | | | | |
| atc | cct | gcc | gat | cca | gga | caa | ctt | gat | tcc | cat | gag | aga | gtt | gtc | cct | 959 |
| Ile | Pro | Ala | Asp | Pro | Gly | Gln | Leu | Asp | Ser | His | Glu | Arg | Val | Val | Pro | |
| | 305 | | | | | 310 | | | | | 315 | | | | | |
| caa | gct | gga | cag | gta | tgg | ttt | cca | gat | tct | gct | aca | aag | aca | gct | cag | 1007 |
| Gln | Ala | Gly | Gln | Val | Trp | Phe | Pro | Asp | Ser | Ala | Thr | Lys | Thr | Ala | Gln | |
| 320 | | | | | 325 | | | | | 330 | | | | | 335 | |
| gca | ata | atg | gat | ttc | aat | agg | gaa | gag | ctt | cca | ctt | ttc | att | ctt | gcc | 1055 |
| Ala | Ile | Met | Asp | Phe | Asn | Arg | Glu | Glu | Leu | Pro | Leu | Phe | Ile | Leu | Ala | |

-continued

```
                    340             345             350
aat tgg aga ggc ttt tct ggt ggg caa agg gat ctt ttt gag ggc atc    1103
Asn Trp Arg Gly Phe Ser Gly Gly Gln Arg Asp Leu Phe Glu Gly Ile
            355             360             365 ctt caa gct gga tca acc att gtt gag aat ctt aga aca tac aaa caa    1151
Leu Gln Ala Gly Ser Thr Ile Val Glu Asn Leu Arg Thr Tyr Lys Gln
            370             375             380 cct gtc ttt gtg tac att ccc atg atg ggt gag ctc cgt ggt ggg gca    1199
Pro Val Phe Val Tyr Ile Pro Met Met Gly Glu Leu Arg Gly Gly Ala
    385             390             395 tgg gtt gtt gtg gac agc cgg atc aat tca gat cat att gaa atg tat    1247
Trp Val Val Val Asp Ser Arg Ile Asn Ser Asp His Ile Glu Met Tyr
400             405             410             415 gct gaa cgc act gct aag ggt aat gta ctt gag cca gaa gga atg att    1295
Ala Glu Arg Thr Ala Lys Gly Asn Val Leu Glu Pro Glu Gly Met Ile
            420             425             430 gaa atc aag ttt agg aca aag gag cta ctg gag tgc atg ggc agg ctt    1343
Glu Ile Lys Phe Arg Thr Lys Glu Leu Leu Glu Cys Met Gly Arg Leu
            435             440             445 gac caa cag ctt ata aac atg aag gca aaa ctt cag gaa gca aag agc    1391
Asp Gln Gln Leu Ile Asn Met Lys Ala Lys Leu Gln Glu Ala Lys Ser
            450             455             460 aat gga gcc cat gca cag atg gat tct ctg cag cag caa ata aga tca    1439
Asn Gly Ala His Ala Gln Met Asp Ser Leu Gln Gln Gln Ile Arg Ser
465             470             475 cgt gag aaa cag ctt tta cca gta tac acc cag ata gcc act aaa ttc    1487
Arg Glu Lys Gln Leu Leu Pro Val Tyr Thr Gln Ile Ala Thr Lys Phe
480             485             490             495 gcc gag ctt cat gat act tct ctg agg atg gca gcg aaa ggg gta ata    1535
Ala Glu Leu His Asp Thr Ser Leu Arg Met Ala Ala Lys Gly Val Ile
            500             505             510 aaa gaa gtg gtt gac tgg gat cgc tca cga tct ttc ttc tat aga aga    1583
Lys Glu Val Val Asp Trp Asp Arg Ser Arg Ser Phe Phe Tyr Arg Arg
            515             520             525 ttg cgc cgg aga att gct gag agt tct ctg gtc aaa att gta aaa aat    1631
Leu Arg Arg Arg Ile Ala Glu Ser Ser Leu Val Lys Ile Val Lys Asn
            530             535             540 gct gct ggt gat caa ctg tcc cat aaa tct gca agg gac ttg atc aaa    1679
Ala Ala Gly Asp Gln Leu Ser His Lys Ser Ala Arg Asp Leu Ile Lys
545             550             555 aaa ggg ttt ttg gat tcc agt gtt gca aag gga aga gaa gat gtt tgg    1727
Lys Gly Phe Leu Asp Ser Ser Val Ala Lys Gly Arg Glu Asp Val Trp
560             565             570             575 gtt aat gat gaa gct ttc ttt tca tgg aag gat gat ctg gga aat tat    1775
Val Asn Asp Glu Ala Phe Phe Ser Trp Lys Asp Asp Leu Gly Asn Tyr
            580             585             590 agt gag aag cta caa gag ctg cgg gtc caa aag gta tta ctt cag ctt    1823
Ser Glu Lys Leu Gln Glu Leu Arg Val Gln Lys Val Leu Leu Gln Leu
            595             600             605 atg aat att ggc aat tca tct tca gat ata caa act cta cct caa ggc    1871
Met Asn Ile Gly Asn Ser Ser Ser Asp Ile Gln Thr Leu Pro Gln Gly
            610             615             620 ctt gct gcc ctt cta agc aag atg gag cca tca agc aga aaa caa atg    1919
Leu Ala Ala Leu Leu Ser Lys Met Glu Pro Ser Ser Arg Lys Gln Met
625             630             635 gtt gat gaa ctt cgt aag gtg ctc ggt tgattaaatt acctataaga           1966
Val Asp Glu Leu Arg Lys Val Leu Gly
640             645 tcctgggttt tctcattctt ctgctacttg cattaatatt ttggtaactt gctgccacac   2026
```

-continued

```
ctggtgtgga tcttctgtaa caattcacgt agcttcatga gaagtggagg tggcagagtc    2086
cttggtgcag ccggtagctt ttgtaagtgt aaaattagca ggttgtagtt gataagagta    2146
ttagattttg tgccgctagg aaatcattgg gcagtctcag tttgatgtgt ttgctgcaga    2206
tgtgatgaaa ctttgctcat atatattaat tttttgaata atggggaagg gagtatcaat    2266
tattcctact tgggaatgca aattcattta agggtgaagg gtattggggc cacttctcct    2326
tgtcctgcat tggttgggga tttgggcttt aaaattttgg atcataaaaa aaaaaatttg    2386
gctaaaaaaa gccccccctt ttcctccttt cccccatgaa aaaggttaaa attttccaaa    2446
gaaaaaaaaa aaaaaaaaat taccaacggg aaggggaat tttcttttag aagtttgtaa     2506
aaaaaaaaaa aaaaaaaaaa aaaaaaaaaa aaaaaaaaaa aaaaaaaaaa aaaaaaaaaa    2566
aaaaaaaaaa aaa                                                       2579
```

<210> SEQ ID NO 10
<211> LENGTH: 648
<212> TYPE: PRT
<213> ORGANISM: Gossypium hirsutum

<400> SEQUENCE: 10

```
Ser Phe Gly Pro Arg Glu Asp Ala Phe Phe Leu Ala Val Thr Asp Leu
1               5                   10                  15

Ala Cys Ser Lys Lys Leu Pro Leu Ile Tyr Leu Ala Ala Asn Ser Gly
            20                  25                  30

Ala Arg Ile Gly Val Ala Glu Glu Val Lys Ala Cys Phe Lys Val Gly
        35                  40                  45

Trp Ser Asn Glu Ser Ser Pro Glu Arg Gly Phe Gln Tyr Val Tyr Leu
    50                  55                  60

Thr Pro Glu Asp Tyr Thr Lys Ile Gly Ser Ser Val Ile Ala His Glu
65                  70                  75                  80

Met Lys Leu Ala Ser Gly Glu Ser Arg Trp Val Ile Asp Thr Ile Val
                85                  90                  95

Gly Lys Glu Asp Gly Leu Gly Val Glu Asn Leu Thr Gly Ser Gly Ala
            100                 105                 110

Ile Ala Gly Ala Tyr Ser Arg Ala Tyr Lys Glu Thr Phe Thr Leu Thr
        115                 120                 125

Tyr Val Thr Gly Arg Thr Val Gly Ile Gly Ala Tyr Leu Ala Arg Leu
    130                 135                 140

Gly Met Arg Cys Ile Gln Arg Leu Asp Gln Pro Ile Ile Leu Thr Gly
145                 150                 155                 160

Phe Ser Ala Leu Asn Lys Leu Leu Gly Arg Glu Val Tyr Ser Ser His
                165                 170                 175

Met Gln Leu Gly Gly Pro Lys Ile Met Ala Thr Asn Gly Val Val His
            180                 185                 190

Leu Thr Val Ser Asp Asp Leu Glu Gly Val Ser Ala Ile Leu Asn Trp
        195                 200                 205

Leu Ser Cys Ile Pro Pro His Ile Gly Gly Pro Leu Pro Ile Leu Asn
    210                 215                 220

Pro Ser Asp Pro Pro Glu Arg Leu Val Glu Tyr Leu Pro Glu Asn Ser
225                 230                 235                 240

Cys Asp Pro Arg Ala Ala Ile Ser Gly Ala Leu Asp Ser Ser Gly Asn
                245                 250                 255

Trp Lys Gly Gly Ile Phe Asp Arg Asp Ser Phe Val Glu Thr Leu Glu
            260                 265                 270
```

-continued

```
Gly Trp Ala Arg Thr Val Val Thr Gly Arg Ala Lys Leu Gly Gly Ile
            275                 280                 285
Pro Val Gly Ile Val Ala Val Glu Thr Gln Thr Val Met Gln Val Ile
        290                 295                 300
Pro Ala Asp Pro Gly Gln Leu Asp Ser His Glu Arg Val Val Pro Gln
305                 310                 315                 320
Ala Gly Gln Val Trp Phe Pro Asp Ser Ala Thr Lys Thr Ala Gln Ala
                325                 330                 335
Ile Met Asp Phe Asn Arg Glu Glu Leu Pro Leu Phe Ile Leu Ala Asn
                    340                 345                 350
Trp Arg Gly Phe Ser Gly Gly Gln Arg Asp Leu Phe Glu Gly Ile Leu
            355                 360                 365
Gln Ala Gly Ser Thr Ile Val Glu Asn Leu Arg Thr Tyr Lys Gln Pro
        370                 375                 380
Val Phe Val Tyr Ile Pro Met Met Gly Glu Leu Arg Gly Gly Ala Trp
385                 390                 395                 400
Val Val Val Asp Ser Arg Ile Asn Ser Asp His Ile Glu Met Tyr Ala
                405                 410                 415
Glu Arg Thr Ala Lys Gly Asn Val Leu Glu Pro Glu Gly Met Ile Glu
                    420                 425                 430
Ile Lys Phe Arg Thr Lys Glu Leu Leu Glu Cys Met Gly Arg Leu Asp
            435                 440                 445
Gln Gln Leu Ile Asn Met Lys Ala Lys Leu Gln Glu Ala Lys Ser Asn
        450                 455                 460
Gly Ala His Ala Gln Met Asp Ser Leu Gln Gln Ile Arg Ser Arg
465                 470                 475                 480
Glu Lys Gln Leu Leu Pro Val Tyr Thr Gln Ile Ala Thr Lys Phe Ala
                485                 490                 495
Glu Leu His Asp Thr Ser Leu Arg Met Ala Ala Lys Gly Val Ile Lys
                    500                 505                 510
Glu Val Val Asp Trp Asp Arg Ser Arg Ser Phe Phe Tyr Arg Arg Leu
            515                 520                 525
Arg Arg Arg Ile Ala Glu Ser Ser Leu Val Lys Ile Val Lys Asn Ala
        530                 535                 540
Ala Gly Asp Gln Leu Ser His Lys Ser Ala Arg Asp Leu Ile Lys Lys
545                 550                 555                 560
Gly Phe Leu Asp Ser Ser Val Ala Lys Gly Arg Glu Asp Val Trp Val
                565                 570                 575
Asn Asp Glu Ala Phe Phe Ser Trp Lys Asp Asp Leu Gly Asn Tyr Ser
                    580                 585                 590
Glu Lys Leu Gln Glu Leu Arg Val Gln Lys Val Leu Leu Gln Leu Met
            595                 600                 605
Asn Ile Gly Asn Ser Ser Ser Asp Ile Gln Thr Leu Pro Gln Gly Leu
        610                 615                 620
Ala Ala Leu Leu Ser Lys Met Glu Pro Ser Ser Arg Lys Gln Met Val
625                 630                 635                 640
Asp Glu Leu Arg Lys Val Leu Gly
                645

<210> SEQ ID NO 11
<211> LENGTH: 679
<212> TYPE: PRT
<213> ORGANISM: Arabidopsis thaliana
```

<400> SEQUENCE: 11

```
Gly Met Val Ala Trp Cys Leu Asp Met Ser Thr Pro Glu Phe Pro Met
1               5                   10                  15

Gly Arg Lys Leu Leu Val Ile Ala Asn Asp Val Thr Phe Lys Ala Gly
            20                  25                  30

Ser Phe Gly Pro Arg Glu Asp Ala Phe Phe Leu Ala Val Thr Glu Leu
        35                  40                  45

Ala Cys Ala Lys Lys Leu Pro Leu Ile Tyr Leu Ala Ala Asn Ser Gly
    50                  55                  60

Ala Arg Leu Gly Val Ala Glu Glu Val Lys Ala Cys Phe Lys Val Gly
65                  70                  75                  80

Trp Ser Asp Glu Ile Ser Pro Glu Asn Gly Phe Gln Tyr Ile Tyr Leu
                85                  90                  95

Ser Pro Glu Asp His Glu Arg Ile Gly Ser Ser Val Ile Ala His Glu
            100                 105                 110

Val Lys Leu Ser Ser Gly Glu Thr Arg Trp Val Ile Asp Thr Ile Val
        115                 120                 125

Gly Lys Glu Asp Gly Ile Gly Val Glu Asn Leu Thr Gly Ser Gly Ala
    130                 135                 140

Ile Ala Gly Ala Tyr Ser Lys Ala Tyr Asn Glu Thr Phe Thr Leu Thr
145                 150                 155                 160

Phe Val Ser Gly Arg Thr Val Gly Ile Gly Ala Tyr Leu Ala Arg Leu
                165                 170                 175

Gly Met Arg Cys Ile Gln Arg Leu Asp Gln Pro Ile Ile Leu Thr Gly
            180                 185                 190

Phe Ser Thr Leu Asn Lys Leu Leu Gly Arg Glu Val Tyr Ser Ser His
        195                 200                 205

Met Gln Leu Gly Gly Pro Lys Ile Met Gly Thr Asn Gly Val Val His
    210                 215                 220

Leu Thr Val Ser Asp Asp Leu Glu Gly Val Ser Ala Ile Leu Asn Trp
225                 230                 235                 240

Leu Ser Tyr Ile Pro Ala Tyr Val Gly Gly Pro Leu Pro Val Leu Ala
                245                 250                 255

Pro Leu Asp Pro Pro Glu Arg Ile Val Glu Tyr Val Pro Glu Asn Ser
            260                 265                 270

Cys Asp Pro Arg Ala Ala Ile Ala Gly Val Lys Asp Asn Thr Gly Lys
        275                 280                 285

Trp Leu Gly Gly Ile Phe Asp Lys Asn Ser Phe Ile Glu Thr Leu Glu
    290                 295                 300

Gly Trp Ala Arg Thr Val Val Thr Gly Arg Ala Lys Leu Gly Gly Ile
305                 310                 315                 320

Pro Val Gly Val Val Ala Val Glu Thr Gln Thr Val Met Gln Ile Ile
                325                 330                 335

Pro Ala Asp Pro Gly Gln Leu Asp Ser His Glu Arg Val Pro Gln
            340                 345                 350

Ala Gly Gln Val Trp Phe Pro Asp Ser Ala Ala Lys Thr Ala Gln Ala
        355                 360                 365

Leu Met Asp Phe Asn Arg Glu Glu Leu Pro Leu Phe Ile Leu Ala Asn
    370                 375                 380

Trp Arg Gly Phe Ser Gly Gly Gln Arg Asp Leu Phe Glu Gly Ile Leu
385                 390                 395                 400

Gln Ala Gly Ser Thr Ile Val Glu Asn Leu Arg Thr Tyr Arg Gln Pro
                405                 410                 415
```

```
Val Phe Val Tyr Ile Pro Met Met Gly Glu Leu Arg Gly Gly Ala Trp
            420                 425                 430

Val Val Val Asp Ser Gln Ile Asn Ser Asp Tyr Val Glu Met Tyr Ala
        435                 440                 445

Asp Glu Thr Ala Arg Gly Asn Val Leu Glu Pro Glu Gly Thr Ile Glu
    450                 455                 460

Ile Lys Phe Arg Thr Lys Glu Leu Leu Glu Cys Met Gly Arg Leu Asp
465                 470                 475                 480

Gln Lys Leu Ile Ser Leu Lys Ala Lys Leu Gln Asp Ala Lys Gln Ser
                485                 490                 495

Glu Ala Tyr Ala Asn Ile Glu Leu Leu Gln Gln Gln Ile Lys Ala Arg
            500                 505                 510

Glu Lys Gln Leu Leu Pro Val Tyr Ile Gln Ile Ala Thr Lys Phe Ala
        515                 520                 525

Glu Leu His Asp Thr Ser Met Arg Met Ala Ala Lys Gly Val Ile Lys
    530                 535                 540

Ser Val Val Glu Trp Ser Gly Ser Arg Ser Phe Phe Tyr Lys Lys Leu
545                 550                 555                 560

Asn Arg Arg Ile Ala Glu Ser Ser Leu Val Lys Asn Val Arg Glu Ala
                565                 570                 575

Ser Gly Asp Asn Leu Ala Tyr Lys Ser Ser Met Arg Leu Ile Gln Asp
            580                 585                 590

Trp Phe Cys Asn Ser Asp Ile Ala Lys Gly Lys Glu Glu Ala Trp Thr
        595                 600                 605

Asp Asp Gln Val Phe Phe Thr Trp Lys Asp Asn Val Ser Asn Tyr Glu
    610                 615                 620

Leu Lys Leu Ser Glu Leu Arg Ala Gln Lys Leu Leu Asn Gln Leu Ala
625                 630                 635                 640

Glu Ile Gly Asn Ser Ser Asp Leu Gln Ala Leu Pro Gln Gly Leu Ala
                645                 650                 655

Asn Leu Leu Asn Lys Val Glu Pro Ser Lys Arg Glu Glu Leu Val Ala
            660                 665                 670

Ala Ile Arg Lys Val Leu Gly
            675

<210> SEQ ID NO 12
<211> LENGTH: 1419
<212> TYPE: DNA
<213> ORGANISM: Gossypium hirsutum
<220> FEATURE:
<221> NAME/KEY: CDS
<222> LOCATION: (1)..(1419)

<400> SEQUENCE: 12 atg gaa gct ctt caa gcc tca tct ctt cga gct tcc cct cta aaa cct      48
Met Glu Ala Leu Gln Ala Ser Ser Leu Arg Ala Ser Pro Leu Lys Pro
1               5                   10                  15 ctc caa aaa ccc aaa ctc aat atc cat ttc ccc aat gca tcg aga ctc      96
Leu Gln Lys Pro Lys Leu Asn Ile His Phe Pro Asn Ala Ser Arg Leu
            20                  25                  30 gtt ccc agg cca acc aag aaa ttc tct tcc atc acc gct tca tcc ccc     144
Val Pro Arg Pro Thr Lys Lys Phe Ser Ser Ile Thr Ala Ser Ser Pro
        35                  40                  45 acc gta tct gct ccc aag cgc gag aag gac ccc aaa aaa cgg gtc gtt     192
Thr Val Ser Ala Pro Lys Arg Glu Lys Asp Pro Lys Lys Arg Val Val
    50                  55                  60
```

```
att acg ggt atg gga ttg gtt tcc gtt ttt ggg aat gat gtc gat gct    240
Ile Thr Gly Met Gly Leu Val Ser Val Phe Gly Asn Asp Val Asp Ala
65              70                  75                  80 tat tac gat aag ttg ctg gct ggg gaa agc ggg atc gga ctc atc gac    288
Tyr Tyr Asp Lys Leu Leu Ala Gly Glu Ser Gly Ile Gly Leu Ile Asp
            85                  90                  95 cgg ttc gat gct tcc aag ttt cct acc cgg ttc gcc ggt cag atc cgg    336
Arg Phe Asp Ala Ser Lys Phe Pro Thr Arg Phe Ala Gly Gln Ile Arg
                100                 105                 110 ggt ttc tct tct cag ggt tac att gac gga aag aac gat agg cga ctt    384
Gly Phe Ser Ser Gln Gly Tyr Ile Asp Gly Lys Asn Asp Arg Arg Leu
            115                 120                 125 gac gat tgc ttg agg tac tgc att gtt gca gga aag aag gct ttg gaa    432
Asp Asp Cys Leu Arg Tyr Cys Ile Val Ala Gly Lys Lys Ala Leu Glu
130                 135                 140 gat gct gat ctc ggg ggc gat aag tta tcc aag atc gat aaa gag cga    480
Asp Ala Asp Leu Gly Gly Asp Lys Leu Ser Lys Ile Asp Lys Glu Arg
145                 150                 155                 160 gct gga gtg cta gtt gga act ggt atg ggt ggt cta acg gtg ttc tct    528
Ala Gly Val Leu Val Gly Thr Gly Met Gly Gly Leu Thr Val Phe Ser
                165                 170                 175 gat ggc gtc caa aat ctg ata gag aaa ggc tat aga aaa ata aca cca    576
Asp Gly Val Gln Asn Leu Ile Glu Lys Gly Tyr Arg Lys Ile Thr Pro
            180                 185                 190 ttc ttc att ccc tat gct ata aca aac atg tca tct gcc ttg cta gcc    624
Phe Phe Ile Pro Tyr Ala Ile Thr Asn Met Ser Ser Ala Leu Leu Ala
        195                 200                 205 att gat ctt ggt ctc atg ggt cca aat tat tca att tca act gct tgt    672
Ile Asp Leu Gly Leu Met Gly Pro Asn Tyr Ser Ile Ser Thr Ala Cys
210                 215                 220 gct acc tcc aat tat tgc ttc tat gct gct gcc aac cac atc cgt cga    720
Ala Thr Ser Asn Tyr Cys Phe Tyr Ala Ala Ala Asn His Ile Arg Arg
225                 230                 235                 240 ggt gag gct gaa atg atg att gct ggt gga act gag gct gca att att    768
Gly Glu Ala Glu Met Met Ile Ala Gly Gly Thr Glu Ala Ala Ile Ile
                245                 250                 255 cct att ggg ctg ggg ggc ttt gtt gcc tgc agg gca ttg tct caa aga    816
Pro Ile Gly Leu Gly Gly Phe Val Ala Cys Arg Ala Leu Ser Gln Arg
            260                 265                 270 aat gat gac cct caa act gct tca aga cca tgg gac aaa gac cga gat    864
Asn Asp Asp Pro Gln Thr Ala Ser Arg Pro Trp Asp Lys Asp Arg Asp
        275                 280                 285 ggc ttt gtt atg ggt gaa ggt gct gga gta ttg gta atg gaa agc ttg    912
Gly Phe Val Met Gly Glu Gly Ala Gly Val Leu Val Met Glu Ser Leu
290                 295                 300 gaa cat gca atg aaa aga ggt gca cca att atc gcc gag tac tta ggt    960
Glu His Ala Met Lys Arg Gly Ala Pro Ile Ile Ala Glu Tyr Leu Gly
305                 310                 315                 320 gga gct gtt aat tgt gat gct tat cat atg act gat cca aga gcc gac   1008
Gly Ala Val Asn Cys Asp Ala Tyr His Met Thr Asp Pro Arg Ala Asp
                325                 330                 335 ggt ctc ggg gtg tct tca tgc atc gag aga agc ctt gaa gat gcc ggt   1056
Gly Leu Gly Val Ser Ser Cys Ile Glu Arg Ser Leu Glu Asp Ala Gly
            340                 345                 350 gtg tcc cct gag gag gtt aat tac atc aat gca cac gcg act tca act   1104
Val Ser Pro Glu Glu Val Asn Tyr Ile Asn Ala His Ala Thr Ser Thr
        355                 360                 365 ctt gct ggt gac ctg gcc gag ata aac gct att aag aag gta ttc aag   1152
Leu Ala Gly Asp Leu Ala Glu Ile Asn Ala Ile Lys Lys Val Phe Lys
370                 375                 380
```

-continued

```
aat aca tct gag atc aaa atc aat gca aca aag tct atg atc ggc cat      1200
Asn Thr Ser Glu Ile Lys Ile Asn Ala Thr Lys Ser Met Ile Gly His
385                 390                 395                 400 tgt ctg ggc gca gca ggt ggt tta gaa gcc att gcc act gtg aaa gcc      1248
Cys Leu Gly Ala Ala Gly Gly Leu Glu Ala Ile Ala Thr Val Lys Ala
                405                 410                 415 att aca act gga tgg gtt cat cca acc att aat caa ttt aat cca gag      1296
Ile Thr Thr Gly Trp Val His Pro Thr Ile Asn Gln Phe Asn Pro Glu
            420                 425                 430 cct tca gtt gag ttc gac act gtt gcc aat gaa aag cag cag cat gag      1344
Pro Ser Val Glu Phe Asp Thr Val Ala Asn Glu Lys Gln Gln His Glu
        435                 440                 445 gtt aac gtt gca ata tcg aat tct ttt cga ttt ggt gga cac aac tct      1392
Val Asn Val Ala Ile Ser Asn Ser Phe Arg Phe Gly Gly His Asn Ser
    450                 455                 460 gtg gtg gca ttt tct gct ttc aag cca                                   1419
Val Val Ala Phe Ser Ala Phe Lys Pro
465                 470
```

<210> SEQ ID NO 13
<211> LENGTH: 473
<212> TYPE: PRT
<213> ORGANISM: Gossypium hirsutum

<400> SEQUENCE: 13

```
Met Glu Ala Leu Gln Ala Ser Ser Leu Arg Ala Ser Pro Leu Lys Pro
1               5                   10                  15

Leu Gln Lys Pro Lys Leu Asn Ile His Phe Pro Asn Ala Ser Arg Leu
            20                  25                  30

Val Pro Arg Pro Thr Lys Lys Phe Ser Ser Ile Thr Ala Ser Ser Pro
        35                  40                  45

Thr Val Ser Ala Pro Lys Arg Glu Lys Asp Pro Lys Lys Arg Val Val
    50                  55                  60

Ile Thr Gly Met Gly Leu Val Ser Val Phe Gly Asn Asp Val Asp Ala
65                  70                  75                  80

Tyr Tyr Asp Lys Leu Leu Ala Gly Glu Ser Gly Ile Gly Leu Ile Asp
                85                  90                  95

Arg Phe Asp Ala Ser Lys Phe Pro Thr Arg Phe Ala Gly Gln Ile Arg
            100                 105                 110

Gly Phe Ser Ser Gln Gly Tyr Ile Asp Gly Lys Asn Asp Arg Arg Leu
        115                 120                 125

Asp Asp Cys Leu Arg Tyr Cys Ile Val Ala Gly Lys Lys Ala Leu Glu
    130                 135                 140

Asp Ala Asp Leu Gly Gly Asp Lys Leu Ser Lys Ile Asp Lys Glu Arg
145                 150                 155                 160

Ala Gly Val Leu Val Gly Thr Gly Met Gly Gly Leu Thr Val Phe Ser
                165                 170                 175

Asp Gly Val Gln Asn Leu Ile Glu Lys Gly Tyr Arg Lys Ile Thr Pro
            180                 185                 190

Phe Phe Ile Pro Tyr Ala Ile Thr Asn Met Ser Ser Ala Leu Leu Ala
        195                 200                 205

Ile Asp Leu Gly Leu Met Gly Pro Asn Tyr Ser Ile Ser Thr Ala Cys
    210                 215                 220

Ala Thr Ser Asn Tyr Cys Phe Tyr Ala Ala Ala Asn His Ile Arg Arg
225                 230                 235                 240

Gly Glu Ala Glu Met Met Ile Ala Gly Gly Thr Glu Ala Ala Ile Ile
```

```
                    245                 250                 255
Pro Ile Gly Leu Gly Gly Phe Val Ala Cys Arg Ala Leu Ser Gln Arg
            260                 265                 270

Asn Asp Asp Pro Gln Thr Ala Ser Arg Pro Trp Asp Lys Asp Arg Asp
        275                 280                 285

Gly Phe Val Met Gly Glu Gly Ala Gly Val Leu Val Met Glu Ser Leu
    290                 295                 300

Glu His Ala Met Lys Arg Gly Ala Pro Ile Ile Ala Glu Tyr Leu Gly
305                 310                 315                 320

Gly Ala Val Asn Cys Asp Ala Tyr His Met Thr Asp Pro Arg Ala Asp
                325                 330                 335

Gly Leu Gly Val Ser Ser Cys Ile Glu Arg Ser Leu Glu Asp Ala Gly
            340                 345                 350

Val Ser Pro Glu Glu Val Asn Tyr Ile Asn Ala His Ala Thr Ser Thr
        355                 360                 365

Leu Ala Gly Asp Leu Ala Glu Ile Asn Ala Ile Lys Lys Val Phe Lys
    370                 375                 380

Asn Thr Ser Glu Ile Lys Ile Asn Ala Thr Lys Ser Met Ile Gly His
385                 390                 395                 400

Cys Leu Gly Ala Ala Gly Gly Leu Glu Ala Ile Ala Thr Val Lys Ala
                405                 410                 415

Ile Thr Thr Gly Trp Val His Pro Thr Ile Asn Gln Phe Asn Pro Glu
            420                 425                 430

Pro Ser Val Glu Phe Asp Thr Val Ala Asn Glu Lys Gln Gln His Glu
        435                 440                 445

Val Asn Val Ala Ile Ser Asn Ser Phe Arg Phe Gly Gly His Asn Ser
    450                 455                 460

Val Val Ala Phe Ser Ala Phe Lys Pro
465                 470

<210> SEQ ID NO 14
<211> LENGTH: 473
<212> TYPE: PRT
<213> ORGANISM: Arabidopsis thaliana

<400> SEQUENCE: 14

Met Gln Ala Leu Gln Ser Ser Ser Leu Arg Ala Ser Pro Pro Asn Pro
1               5                   10                  15

Leu Arg Leu Pro Ser Asn Arg Gln Ser His Gln Leu Ile Thr Asn Ala
            20                  25                  30

Arg Pro Leu Arg Arg Gln Gln Arg Ser Phe Ile Ser Ala Ser Ala Ser
        35                  40                  45

Thr Val Ser Ala Pro Lys Arg Glu Thr Asp Pro Lys Lys Arg Val Val
    50                  55                  60

Ile Thr Gly Met Gly Leu Val Ser Val Phe Gly Asn Asp Val Asp Ala
65                  70                  75                  80

Tyr Tyr Glu Lys Leu Leu Ser Gly Glu Ser Gly Ile Ser Leu Ile Asp
                85                  90                  95

Arg Phe Asp Ala Ser Lys Phe Pro Thr Arg Phe Gly Gly Gln Ile Arg
            100                 105                 110

Gly Phe Ser Ser Glu Gly Tyr Ile Asp Gly Lys Asn Glu Arg Arg Leu
        115                 120                 125

Asp Asp Cys Leu Lys Tyr Cys Ile Val Ala Gly Lys Lys Ala Leu Glu
    130                 135                 140
```

Ser Ala Asn Leu Gly Gly Asp Lys Leu Asn Thr Ile Asp Lys Arg Lys
145                 150                 155                 160

Ala Gly Val Leu Val Gly Thr Gly Met Gly Gly Leu Thr Val Phe Ser
            165                 170                 175

Glu Gly Val Gln Asn Leu Ile Glu Lys Gly His Arg Arg Ile Ser Pro
            180                 185                 190

Phe Phe Ile Pro Tyr Ala Ile Thr Asn Met Gly Ser Ala Leu Leu Ala
            195                 200                 205

Ile Asp Leu Gly Leu Met Gly Pro Asn Tyr Ser Ile Ser Thr Ala Cys
210                 215                 220

Ala Thr Ser Asn Tyr Cys Phe Tyr Ala Ala Asn His Ile Arg Arg
225                 230                 235                 240

Gly Glu Ala Asp Met Met Ile Ala Gly Gly Thr Glu Ala Ala Ile Ile
                245                 250                 255

Pro Ile Gly Leu Gly Gly Phe Val Ala Cys Arg Ala Leu Ser Gln Arg
            260                 265                 270

Asn Asp Asp Pro Gln Thr Ala Ser Arg Pro Trp Asp Lys Ala Arg Asp
            275                 280                 285

Gly Phe Val Met Gly Glu Gly Ala Gly Val Leu Val Met Glu Ser Leu
290                 295                 300

Glu His Ala Met Lys Arg Gly Ala Pro Ile Val Ala Glu Tyr Leu Gly
305                 310                 315                 320

Gly Ala Val Asn Cys Asp Ala His His Met Thr Asp Pro Arg Ala Asp
                325                 330                 335

Gly Leu Gly Val Ser Ser Cys Ile Glu Arg Cys Leu Glu Asp Ala Gly
            340                 345                 350

Val Ser Pro Glu Glu Val Asn Tyr Ile Asn Ala His Ala Thr Ser Thr
            355                 360                 365

Leu Ala Gly Asp Leu Ala Glu Ile Asn Ala Ile Lys Lys Val Phe Lys
370                 375                 380

Ser Thr Ser Gly Ile Lys Ile Asn Ala Thr Lys Ser Met Ile Gly His
385                 390                 395                 400

Cys Leu Gly Ala Ala Gly Gly Leu Glu Ala Ile Ala Thr Val Lys Ala
                405                 410                 415

Ile Asn Thr Gly Trp Leu His Pro Ser Ile Asn Gln Phe Asn Pro Glu
            420                 425                 430

Gln Ala Val Asp Phe Asp Thr Val Pro Asn Glu Lys Lys Gln His Glu
            435                 440                 445

Val Asp Val Ala Ile Ser Asn Ser Phe Gly Phe Gly Gly His Asn Ser
            450                 455                 460

Val Val Ala Phe Ser Ala Phe Lys Pro
465                 470

<210> SEQ ID NO 15
<211> LENGTH: 1674
<212> TYPE: DNA
<213> ORGANISM: Gossypium hirsutum
<220> FEATURE:
<221> NAME/KEY: CDS
<222> LOCATION: (1)..(1671)

<400> SEQUENCE: 15 atg tcg gta acg tac ggt aaa gac cag tcc cgg tct cca ttg ttc aac    48
Met Ser Val Thr Tyr Gly Lys Asp Gln Ser Arg Ser Pro Leu Phe Asn
1               5                   10                  15 tca tca gcc tcc gct tct tcg aac agg ctc ggc cgt tgg gct cgt aat    96

```
        Ser Ser Ala Ser Ala Ser Ser Asn Arg Leu Gly Arg Trp Ala Arg Asn
                    20                  25                  30 aga agg aag gct ctc ctt tct caa tgc tgt ggt ggc ggc gca acc cct        144
Arg Arg Lys Ala Leu Leu Ser Gln Cys Cys Gly Gly Gly Ala Thr Pro
            35                  40                  45 aac aaa gac gtg ggc ttg att tct tcc ttc cgt gga tcc acc att caa        192
Asn Lys Asp Val Gly Leu Ile Ser Ser Phe Arg Gly Ser Thr Ile Gln
        50                  55                  60 ggc ttg atg gct tct tgc ttg gct ttt gag cct tgt gat gat tat tat        240
Gly Leu Met Ala Ser Cys Leu Ala Phe Glu Pro Cys Asp Asp Tyr Tyr
65                  70                  75                  80 tcc tcc aaa aat ggt agc ttt ttc ggt caa aat gga agc ttt tca tct        288
Ser Ser Lys Asn Gly Ser Phe Phe Gly Gln Asn Gly Ser Phe Ser Ser
                85                  90                  95 ttc ttc ggc tcc aaa aat gtt cct ttc aat aaa aat cgc aag caa aaa        336
Phe Phe Gly Ser Lys Asn Val Pro Phe Asn Lys Asn Arg Lys Gln Lys
            100                 105                 110 agg ctc aat cga cga gct cat cat tct gga caa gcc atg gct ata gct        384
Arg Leu Asn Arg Arg Ala His His Ser Gly Gln Ala Met Ala Ile Ala
        115                 120                 125 gtg caa ccc aca aga gag att aca acg aag aag aag cct cct acg aag        432
Val Gln Pro Thr Arg Glu Ile Thr Thr Lys Lys Lys Pro Pro Thr Lys
130                 135                 140 caa aga cga gtg gtt gtg act ggg atg gga gta gta act ccg ctt gga        480
Gln Arg Arg Val Val Val Thr Gly Met Gly Val Val Thr Pro Leu Gly
145                 150                 155                 160 cat gag cct gat gtt ttc tat aac aac ctg ctt gag ggt gtt agt ggt        528
His Glu Pro Asp Val Phe Tyr Asn Asn Leu Leu Glu Gly Val Ser Gly
                165                 170                 175 ata agt gaa atc gag act ttt gac tgc gct cag ttt ccg aca agg att        576
Ile Ser Glu Ile Glu Thr Phe Asp Cys Ala Gln Phe Pro Thr Arg Ile
            180                 185                 190 gct gga gag atc aaa tct ttc tca act gat gga tgg gtc gca ccg aaa        624
Ala Gly Glu Ile Lys Ser Phe Ser Thr Asp Gly Trp Val Ala Pro Lys
        195                 200                 205 ctt tcc aag agg atg gac aaa ttc atg ctt tat tct ctt act gcc gga        672
Leu Ser Lys Arg Met Asp Lys Phe Met Leu Tyr Ser Leu Thr Ala Gly
210                 215                 220 aag aaa gct ttg caa gat ggg gga gta aat gaa gat gta atg gag gag        720
Lys Lys Ala Leu Gln Asp Gly Gly Val Asn Glu Asp Val Met Glu Glu
225                 230                 235                 240 tta gat aaa acg aaa tgc gga gtt ttg att ggt tca gca atg ggt ggc        768
Leu Asp Lys Thr Lys Cys Gly Val Leu Ile Gly Ser Ala Met Gly Gly
                245                 250                 255 atg aag gtt ttc aat gat gcg att gaa gct ttg agg atc tca tac agg        816
Met Lys Val Phe Asn Asp Ala Ile Glu Ala Leu Arg Ile Ser Tyr Arg
            260                 265                 270 aag atg aat cct ttt tgc gta ccg ttt gct aca aca aat atg ggt tct        864
Lys Met Asn Pro Phe Cys Val Pro Phe Ala Thr Thr Asn Met Gly Ser
        275                 280                 285 gca atg ctt gca atg gat ttg gga tgg atg ggt cct aat tat tca atc        912
Ala Met Leu Ala Met Asp Leu Gly Trp Met Gly Pro Asn Tyr Ser Ile
290                 295                 300 tcc act gca tgt gct aca agc aac ttt tgc ata tta aat gca gca aac        960
Ser Thr Ala Cys Ala Thr Ser Asn Phe Cys Ile Leu Asn Ala Ala Asn
305                 310                 315                 320 cat atc att aga ggc gaa gct gat atg atg ctt tgt ggt ggc tcc gat       1008
His Ile Ile Arg Gly Glu Ala Asp Met Met Leu Cys Gly Gly Ser Asp
                325                 330                 335
```

```
gca gcg att ata ccc att ggt ttg ggg gga ttt gtg gct tgt aga gcg    1056
Ala Ala Ile Ile Pro Ile Gly Leu Gly Gly Phe Val Ala Cys Arg Ala
        340                 345                 350 ctt tct cag agg aac aat gat cct acc aaa gct tca cgc cct tgg gat    1104
Leu Ser Gln Arg Asn Asn Asp Pro Thr Lys Ala Ser Arg Pro Trp Asp
            355                 360                 365 gct aat cgc gat gga ttt gtc atg ggg gaa ggt gct ggg gtt cta ctt    1152
Ala Asn Arg Asp Gly Phe Val Met Gly Glu Gly Ala Gly Val Leu Leu
    370                 375                 380 ttg gaa gaa ttg gag cat gct aag agg aga ggt gcg act atc tat gca    1200
Leu Glu Glu Leu Glu His Ala Lys Arg Arg Gly Ala Thr Ile Tyr Ala
385                 390                 395                 400 gaa ttc ctt ggt gga agc ttc act tgt gat gct tat cac atg acc gag    1248
Glu Phe Leu Gly Gly Ser Phe Thr Cys Asp Ala Tyr His Met Thr Glu
                405                 410                 415 cct cac cct gat ggt gtt ggt gtc att ctc tgc atc gaa aag gcc ttg    1296
Pro His Pro Asp Gly Val Gly Val Ile Leu Cys Ile Glu Lys Ala Leu
            420                 425                 430 gct cac gct ggt gta tct aga gga gat ata aac tat att aat gct cat    1344
Ala His Ala Gly Val Ser Arg Gly Asp Ile Asn Tyr Ile Asn Ala His
    435                 440                 445 gct aca tcg aca cca act gga gac att aaa gaa tac caa gct ctt ctt    1392
Ala Thr Ser Thr Pro Thr Gly Asp Ile Lys Glu Tyr Gln Ala Leu Leu
450                 455                 460 cat tgt ttt gga gaa aat ccc gag tta agg gtg aac tct aca aaa tca    1440
His Cys Phe Gly Glu Asn Pro Glu Leu Arg Val Asn Ser Thr Lys Ser
465                 470                 475                 480 atg att ggt cac cta cta gga gct tcc ggt gct gtg gaa gct gtt gca    1488
Met Ile Gly His Leu Leu Gly Ala Ser Gly Ala Val Glu Ala Val Ala
                485                 490                 495 acg gta cag gca ata cga act ggt tgg gtt cat cca aat atc aac ctg    1536
Thr Val Gln Ala Ile Arg Thr Gly Trp Val His Pro Asn Ile Asn Leu
            500                 505                 510 gaa aac ccg gac gta gga gtg gac aca agt gtg ctt gtg ggg cca aat    1584
Glu Asn Pro Asp Val Gly Val Asp Thr Ser Val Leu Val Gly Pro Asn
    515                 520                 525 aaa gaa aga ttg aac gtt aag gcg gca ttg tcg aat tca ttc ggg ttt    1632
Lys Glu Arg Leu Asn Val Lys Ala Ala Leu Ser Asn Ser Phe Gly Phe
530                 535                 540 ggc ggg cat aac tca tcg atc att ttc gcc cca tac aag taa             1674
Gly Gly His Asn Ser Ser Ile Ile Phe Ala Pro Tyr Lys
545                 550                 555
```

<210> SEQ ID NO 16
<211> LENGTH: 557
<212> TYPE: PRT
<213> ORGANISM: Gossypium hirsutum

<400> SEQUENCE: 16

```
Met Ser Val Thr Tyr Gly Lys Asp Gln Ser Arg Ser Pro Leu Phe Asn
1               5                   10                  15

Ser Ser Ala Ser Ala Ser Asn Arg Leu Gly Arg Trp Ala Arg Asn
            20                  25                  30

Arg Arg Lys Ala Leu Leu Ser Gln Cys Cys Gly Gly Ala Thr Pro
        35                  40                  45

Asn Lys Asp Val Gly Leu Ile Ser Ser Phe Arg Gly Ser Thr Ile Gln
    50                  55                  60

Gly Leu Met Ala Ser Cys Leu Ala Phe Glu Pro Cys Asp Asp Tyr Tyr
65                  70                  75                  80
```

```
Ser Ser Lys Asn Gly Ser Phe Phe Gly Gln Asn Gly Ser Phe Ser Ser
             85                  90                  95

Phe Phe Gly Ser Lys Asn Val Pro Phe Asn Lys Asn Arg Lys Gln Lys
            100                 105                 110

Arg Leu Asn Arg Arg Ala His His Ser Gly Gln Ala Met Ala Ile Ala
            115                 120                 125

Val Gln Pro Thr Arg Glu Ile Thr Thr Lys Lys Pro Pro Thr Lys
130             135                 140

Gln Arg Arg Val Val Val Thr Gly Met Gly Val Val Thr Pro Leu Gly
145             150                 155                 160

His Glu Pro Asp Val Phe Tyr Asn Asn Leu Leu Glu Gly Val Ser Gly
                165                 170                 175

Ile Ser Glu Ile Glu Thr Phe Asp Cys Ala Gln Phe Pro Thr Arg Ile
            180                 185                 190

Ala Gly Glu Ile Lys Ser Phe Ser Thr Asp Gly Trp Val Ala Pro Lys
            195                 200                 205

Leu Ser Lys Arg Met Asp Lys Phe Met Leu Tyr Ser Leu Thr Ala Gly
    210                 215                 220

Lys Lys Ala Leu Gln Asp Gly Gly Val Asn Glu Asp Val Met Glu Glu
225             230                 235                 240

Leu Asp Lys Thr Lys Cys Gly Val Leu Ile Gly Ser Ala Met Gly Gly
            245                 250                 255

Met Lys Val Phe Asn Asp Ala Ile Glu Ala Leu Arg Ile Ser Tyr Arg
            260                 265                 270

Lys Met Asn Pro Phe Cys Val Pro Phe Ala Thr Thr Asn Met Gly Ser
            275                 280                 285

Ala Met Leu Ala Met Asp Leu Gly Trp Met Gly Pro Asn Tyr Ser Ile
    290                 295                 300

Ser Thr Ala Cys Ala Thr Ser Asn Phe Cys Ile Leu Asn Ala Ala Asn
305             310                 315                 320

His Ile Ile Arg Gly Glu Ala Asp Met Met Leu Cys Gly Gly Ser Asp
            325                 330                 335

Ala Ala Ile Ile Pro Ile Gly Leu Gly Gly Phe Val Ala Cys Arg Ala
            340                 345                 350

Leu Ser Gln Arg Asn Asn Asp Pro Thr Lys Ala Ser Arg Pro Trp Asp
    355                 360                 365

Ala Asn Arg Asp Gly Phe Val Met Gly Glu Gly Ala Gly Val Leu Leu
    370                 375                 380

Leu Glu Glu Leu Glu His Ala Lys Arg Arg Gly Ala Thr Ile Tyr Ala
385             390                 395                 400

Glu Phe Leu Gly Gly Ser Phe Thr Cys Asp Ala Tyr His Met Thr Glu
                405                 410                 415

Pro His Pro Asp Gly Val Gly Val Ile Leu Cys Ile Glu Lys Ala Leu
            420                 425                 430

Ala His Ala Gly Val Ser Arg Gly Asp Ile Asn Tyr Ile Asn Ala His
            435                 440                 445

Ala Thr Ser Thr Pro Thr Gly Asp Ile Lys Glu Tyr Gln Ala Leu Leu
    450                 455                 460

His Cys Phe Gly Glu Asn Pro Glu Leu Arg Val Asn Ser Thr Lys Ser
465             470                 475                 480

Met Ile Gly His Leu Leu Gly Ala Ser Gly Ala Val Glu Ala Val Ala
            485                 490                 495

Thr Val Gln Ala Ile Arg Thr Gly Trp Val His Pro Asn Ile Asn Leu
```

```
                500                 505                 510
Glu Asn Pro Asp Val Gly Val Asp Thr Ser Val Leu Val Gly Pro Asn
            515                 520                 525

Lys Glu Arg Leu Asn Val Lys Ala Ala Leu Ser Asn Ser Phe Gly Phe
        530                 535                 540

Gly Gly His Asn Ser Ser Ile Ile Phe Ala Pro Tyr Lys
545                 550                 555

<210> SEQ ID NO 17
<211> LENGTH: 521
<212> TYPE: PRT
<213> ORGANISM: Arabidopsis thaliana

<400> SEQUENCE: 17

Met Ser Val Ser His Gly Gly Asp Ser Arg Gln Ala Val Ala Leu
1               5                   10                  15

Gln Ser Gly Gly Arg Ser Arg Arg Arg Gln Leu Ser Lys Cys Ser
            20                  25                  30

Val Ala Ser Gly Ser Ala Ser Ile Gln Ala Leu Val Thr Ser Cys Leu
            35                  40                  45

Asp Phe Gly Pro Cys Thr His Tyr Asn Asn Asn Ala Leu Ser Ser
    50                  55                  60

Leu Phe Gly Ser Asn Ser Val Ser Leu Asn Arg Asn Gln Arg Arg Leu
65                  70                  75                  80

Asn Arg Ala Ala Ser Ser Gly Gly Ala Met Ala Val Met Glu Met Glu
                85                  90                  95

Lys Glu Ala Ala Val Asn Lys Lys Pro Pro Thr Glu Gln Arg Arg Val
            100                 105                 110

Val Val Thr Gly Met Gly Val Glu Thr Ser Leu Gly His Asp Pro His
            115                 120                 125

Thr Phe Tyr Glu Asn Leu Leu Gln Gly Asn Ser Gly Ile Ser Gln Ile
    130                 135                 140

Glu Asn Phe Asp Cys Ser Glu Phe Pro Thr Arg Ile Ala Gly Glu Ile
145                 150                 155                 160

Lys Ser Phe Ser Thr Glu Gly Trp Val Ala Pro Lys Leu Ser Lys Arg
                165                 170                 175

Met Asp Lys Phe Met Leu Tyr Leu Leu Thr Ala Gly Lys Lys Ala Leu
            180                 185                 190

Ala Asp Gly Gly Val Thr Asp Glu Val Met Ala Glu Phe Asp Lys Thr
        195                 200                 205

Lys Cys Gly Val Leu Ile Gly Ser Ala Met Gly Gly Met Lys Val Phe
    210                 215                 220

Tyr Asp Ala Ile Glu Ala Leu Arg Ile Ser Tyr Lys Lys Met Asn Pro
225                 230                 235                 240

Phe Cys Val Pro Phe Ala Thr Thr Asn Met Gly Ser Ala Met Leu Ala
                245                 250                 255

Met Asp Leu Gly Trp Met Gly Pro Asn Tyr Ser Ile Ser Thr Ala Cys
            260                 265                 270

Ala Thr Ser Asn Phe Cys Ile Leu Asn Ser Ala Asn His Ile Ile Lys
        275                 280                 285

Gly Glu Ala Asp Val Met Leu Cys Gly Gly Ser Asp Ala Val Ile Ile
    290                 295                 300

Pro Ile Gly Leu Gly Gly Phe Val Ala Cys Arg Ala Leu Ser Gln Arg
305                 310                 315                 320
```

```
Asn Asn Asp Pro Thr Lys Ala Ser Arg Pro Trp Asp Thr Asn Arg Asp
                325                 330                 335

Gly Phe Val Met Gly Glu Gly Ala Gly Val Leu Leu Leu Glu Glu Leu
            340                 345                 350

Glu His Ala Lys Lys Arg Gly Ala Thr Ile Tyr Ala Glu Phe Leu Gly
        355                 360                 365

Gly Ser Phe Thr Cys Asp Ala Tyr His Met Thr Glu Pro His Pro Asp
    370                 375                 380

Gly Ala Gly Val Ile Leu Cys Ile Glu Arg Ala Leu Ala Ser Ala Gly
385                 390                 395                 400

Ile Ser Lys Glu Gln Ile Asn Tyr Ile Asn Ala His Ala Thr Ser Thr
                405                 410                 415

His Ala Gly Asp Ile Lys Glu Tyr Gln Ala Leu Ala His Cys Phe Gly
            420                 425                 430

Gln Asn Pro Glu Leu Lys Val Asn Ser Thr Lys Ser Met Ile Gly His
        435                 440                 445

Leu Leu Gly Ala Ala Gly Ala Val Glu Ala Val Ala Thr Val Gln Ala
    450                 455                 460

Ile Arg Thr Gly Trp Val His Pro Asn Ile Asn Leu Glu Asn Pro Asp
465                 470                 475                 480

Ser Gly Val Asp Thr Lys Leu Leu Val Gly Pro Lys Lys Glu Arg Leu
                485                 490                 495

Asp Ile Lys Ala Ala Leu Ser Asn Ser Phe Gly Phe Gly Gly His Asn
            500                 505                 510

Ser Ser Ile Ile Phe Ala Pro Tyr Lys
        515                 520

<210> SEQ ID NO 18
<211> LENGTH: 554
<212> TYPE: PRT
<213> ORGANISM: Jatropha curcas

<400> SEQUENCE: 18

Met Ser Val Thr Cys Ala Lys Glu Asn Arg Thr Ala Pro His Ala Phe
1               5                   10                  15

His Ser Ser Gln Pro Ser Asn Arg Leu Ser Arg Trp Ala Arg Arg Arg
            20                  25                  30

Lys Thr Leu His Ala Gln Tyr Asn Ser Asp Ser Ser Asn Ser Ile Ala
        35                  40                  45

Ala Gly Gly Gly Gly Gly Gly Gly Tyr Ser Thr Glu Phe Leu
    50                  55                  60

Ser Asn Ser Leu Val Ser Thr Leu Cys Gly Ser Ser Phe Gln Gly Leu
65                  70                  75                  80

Met Ser Ser Cys Leu Ala Phe Glu Pro Cys Ser Gln Tyr Tyr Ser Ser
                85                  90                  95

Asn Gly Leu Phe Arg Ser Arg Asn Leu Asn Arg Lys Gln Arg Arg Leu
            100                 105                 110

Asn Arg Leu Ala Leu Ser Gly Glu Ala Met Ala Ile Ala Val Gln Pro
        115                 120                 125

Glu Lys Glu Val Ala Thr Lys Lys Pro Ala Thr Lys Gln Arg Arg
    130                 135                 140

Val Val Val Thr Gly Met Gly Val Val Ser Pro Leu Gly His Glu Pro
145                 150                 155                 160

Asp Val Phe Tyr Asn Asn Leu Leu Glu Gly Val Ser Gly Ile Ser Gln
                165                 170                 175
```

Ile Glu Ala Phe Glu Cys Ala Gln Phe Pro Thr Arg Ile Ala Gly Glu
            180                 185                 190

Ile Lys Ser Phe Ser Thr Asp Gly Trp Ile Ala Pro Lys Leu Ser Lys
        195                 200                 205

Arg Met Asp Lys Phe Met Leu Tyr Met Leu Thr Ala Gly Lys Lys Ala
    210                 215                 220

Leu Ala Asp Gly Gly Ile Thr Glu Asp Ile Met Asp Glu Leu Asp Lys
225                 230                 235                 240

Ala Lys Cys Gly Val Leu Ile Gly Ser Ala Met Gly Gly Met Lys Val
                245                 250                 255

Phe Asn Asp Ala Ile Glu Ala Leu Arg Val Ser Tyr Arg Lys Met Asn
            260                 265                 270

Pro Phe Cys Val Pro Phe Ala Thr Thr Asn Met Gly Ser Ala Met Leu
        275                 280                 285

Ala Met Asp Leu Gly Trp Met Gly Pro Asn Tyr Ser Ile Ser Thr Ala
    290                 295                 300

Cys Ala Thr Ser Asn Phe Cys Ile Leu Asn Ala Ala Asn His Ile Ile
305                 310                 315                 320

Arg Gly Glu Ala Asp Ile Met Leu Cys Gly Gly Ser Asp Ala Ala Ile
                325                 330                 335

Ile Pro Ile Gly Leu Gly Gly Phe Val Ala Cys Arg Ala Leu Ser Gln
            340                 345                 350

Arg Asn Asp Asp Pro Ala Lys Ala Ser Arg Pro Trp Asp Met Asn Arg
        355                 360                 365

Asp Gly Phe Val Met Gly Glu Gly Ala Gly Val Leu Leu Leu Glu Glu
    370                 375                 380

Leu Glu His Ala Lys Lys Arg Gly Ala Asn Ile Tyr Ala Glu Phe Leu
385                 390                 395                 400

Gly Gly Ser Phe Thr Cys Asp Ala Tyr His Met Thr Glu Pro Arg Pro
                405                 410                 415

Gly Gly Ile Gly Val Ile Leu Cys Val Glu Lys Ala Leu Ala Gln Ser
            420                 425                 430

Gly Val Ser Arg Glu Asp Val Asn Tyr Ile Asn Ala His Ala Thr Ser
        435                 440                 445

Thr Pro Ala Gly Asp Ile Lys Glu Phe Gly Ala Leu Met His Cys Phe
    450                 455                 460

Gly Gln Asn Pro Gly Leu Arg Val Asn Ser Thr Lys Ser Met Ile Gly
465                 470                 475                 480

His Leu Leu Gly Ala Ala Gly Ala Val Glu Ala Ile Ala Ala Ile Gln
                485                 490                 495

Ala Ile Arg Thr Gly Trp Val His Pro Asn Ile Asn Leu Glu Asn Pro
            500                 505                 510

Asp Glu Gly Val Asp Thr Asn Val Leu Val Gly Pro Lys Lys Glu Arg
        515                 520                 525

Leu Asp Val Lys Val Ala Leu Ser Asn Ser Phe Gly Phe Gly Gly His
    530                 535                 540

Asn Ser Ser Ile Val Phe Ala Pro His Lys
545                 550

<210> SEQ ID NO 19
<211> LENGTH: 27
<212> TYPE: DNA
<213> ORGANISM: Gossypium hirsutum

<400> SEQUENCE: 19
ggttttctag aggagtttct aagtatc                                27

<210> SEQ ID NO 20
<211> LENGTH: 33
<212> TYPE: DNA
<213> ORGANISM: Gossypium hirsutum

<400> SEQUENCE: 20
cgtatggatc ccatggagag ggattccggg acc                         33

<210> SEQ ID NO 21
<211> LENGTH: 34
<212> TYPE: DNA
<213> ORGANISM: Gossypium hirsutum

<400> SEQUENCE: 21
atatatctag aggctttgtt atgggtgaag gtgc                        34

<210> SEQ ID NO 22
<211> LENGTH: 35
<212> TYPE: DNA
<213> ORGANISM: Gossypium hirsutum

<400> SEQUENCE: 22
gtcatggatc ctgccaccac agagttgtgt ccacc                       35

<210> SEQ ID NO 23
<211> LENGTH: 33
<212> TYPE: DNA
<213> ORGANISM: Gossypium hirsutum

<400> SEQUENCE: 23
aataatctag agaggatctc atacaggaag atg                         33

<210> SEQ ID NO 24
<211> LENGTH: 32
<212> TYPE: DNA
<213> ORGANISM: Gossypium hirsutum

<400> SEQUENCE: 24
atgctggatc cacaccagcg tgagccaagg cc                          32

<210> SEQ ID NO 25
<211> LENGTH: 33
<212> TYPE: DNA
<213> ORGANISM: Gossypium hirsutum

<400> SEQUENCE: 25
ataattctag agcatacaga gactcgatca acc                         33

<210> SEQ ID NO 26
<211> LENGTH: 36
<212> TYPE: DNA
<213> ORGANISM: Gossypium hirsutum

<400> SEQUENCE: 26
ttgaaaggat cccccctcaaa aagatcccctt tgccca                    36

<210> SEQ ID NO 27
<211> LENGTH: 20
<212> TYPE: DNA
<213> ORGANISM: Gossypium hirsutum -continued

```
<400> SEQUENCE: 27
caacgctcca tcttgtcctt                                          20

<210> SEQ ID NO 28
<211> LENGTH: 20
<212> TYPE: DNA
<213> ORGANISM: Gossypium hirsutum

<400> SEQUENCE: 28
tgatcgtctt tcccgtaagc                                          20

<210> SEQ ID NO 29
<211> LENGTH: 24
<212> TYPE: DNA
<213> ORGANISM: Arabidopsis thaliana

<400> SEQUENCE: 29
ggcacgaggg gggaagaaaa aaaa                                     24

<210> SEQ ID NO 30
<211> LENGTH: 22
<212> TYPE: DNA
<213> ORGANISM: Arabidopsis thaliana

<400> SEQUENCE: 30
taacccgaaa catcaaccat ta                                       22
```